US008313740B2

(12) United States Patent
Delcayre et al.

(10) Patent No.: US 8,313,740 B2
(45) Date of Patent: *Nov. 20, 2012

(54) METHODS FOR TREATING CANCER WITH A RECOMBINANT MVA EXPRESSING HER-2

(75) Inventors: Alain Delcayre, San Jose, CA (US); Reiner Laus, Saratoga, CA (US); Stefanie Mandl, San Francisco, CA (US)

(73) Assignee: BN ImmunoTherapeutics, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/872,156

(22) Filed: Aug. 31, 2010

(65) Prior Publication Data

US 2011/0008294 A1 Jan. 13, 2011

Related U.S. Application Data

(63) Continuation of application No. 11/905,876, filed on Oct. 5, 2007, now Pat. No. 7,807,146.

(60) Provisional application No. 60/850,031, filed on Oct. 6, 2006.

(51) Int. Cl.
*A61K 31/70* (2006.01)
*A61K 48/00* (2006.01)
*A01N 43/04* (2006.01)

(52) U.S. Cl. ..................................... 424/93.2; 514/44 R

(58) Field of Classification Search ........................ None
See application file for complete search history.

(56) References Cited

U.S. PATENT DOCUMENTS

| | | | |
|---|---|---|---|
| 6,683,059 B1 | 1/2004 | Hung et al. | |
| 6,761,893 B2 | 7/2004 | Chaplin et al. | |
| 6,913,752 B2 | 7/2005 | Chaplin et al. | |
| 7,005,498 B1 | 2/2006 | Steinaa et al. | |
| 7,807,146 B2 * | 10/2010 | Delcayre et al. ............. | 424/93.2 |
| 2004/0141958 A1 | 7/2004 | Steinaa et al. | |
| 2006/0008465 A1 | 1/2006 | Steinaa et al. | |
| 2006/0240511 A1 | 10/2006 | Eskling et al. | |
| 2008/0213302 A1 | 9/2008 | Delcayre et al. | |

FOREIGN PATENT DOCUMENTS

| | | |
|---|---|---|
| EP | 1188834 A1 | 3/2002 |
| WO | 95/05849 A1 | 3/1995 |
| WO | 2004/058278 A1 | 7/2004 |
| WO | 2006/089690 A1 | 8/2006 |

OTHER PUBLICATIONS

Antonia et al., "Combination of p53 Cancer Vaccine with Chemotherapy in Patients with Extensive Stage Small Cell Lung Cancer" Clin Cancer Res, 2006, 12:878-887.
Arlen et al., "Pox Viral Vaccine Approaches" Semin Oncology, 2005, 32:549-555.
Arlen et al., "A Randomized Phase II Study of Concurrent Docetaxel Plus Vaccine Versus Vaccine Alone in Metastatic Androgen-Independent Prostate Cancer" Clin Cancer Res, 2006, 12:1260-1269.
Arlen et al., "A Randomized Phase II Study of Docetaxel Alone or in Combination with PANVAC-V (Vaccinia) and PANVAC-F (Fowlpox) in Patients with Metastatic Breast Cancer (NCI 05-C-0229)" Clinical Breast Cancer, 2006, 7:176-179.
Chong et al., "Combining cancer vaccines with chemotherapy" Expert Opinion Pharmacother, 2005, 2813-2820.
Chu et al., "Efficacy of GM-CSF-producing Tumor Vaccine after Docetaxel Chemotherapy in Mice Bearing Established Lewis Lung Carcinoma" J Immunother, 2006, 29:367-380.
Dela Cruz et al., "Insights into the mechanism of anti-tumor immunity in mice vaccinated with the human HER2/neu extracellular domain plus anti-HER2/neu IgG3-(IL-2) or anti-HER2/neu IgG3-(GM-CSF) fusion protein" Vaccine, 2005, 23:4793-4803.
Emens et al., "Breast cancer vaccines: maximizing cancer treatment by tapping into host immunity" Endocrine-Related Cancer, 2005, 12:1-17.
Harrop et al., "Viral Vectors for Cancer Immunotherapy" Frontiers in Bioscience, 2006, 11:804-817.
Liu et al., "Gene-based vaccines and immunotherapeutics" Proc. Natl. Acad. Sci. USA, 2004, 101 (Suppl. 2):14567-14571.
Machiels et al., "Cyclophosphamide, Doxorubicin, and Paclitaxel Enhance the Antitumor Immune Response of Granulocyte/Macrophage-Colony Stimulating Factor-secreting Whole-Cell Vaccines in HER-2/neu Tolerized Mice" Cancer Research, 2001, 61:3689-3697.
Mittendorf et al., "Evaluation of the HER2/neu-Derived Peptide GP2 for Use in a Peptide-Based Breast Cancer Vaccine Trial" Cancer, 2006, 106:2309-2317.
Prell et al., "The anti-tumor efficacy of a GM-CSF-secreting tumor cell vaccine is not inhibited by docetaxel administration" Cancer Immunol Immunother, 2006, 55:1285-1293.
Renard et al., "HER-2 DNA and Protein Vaccines Containing Potent Th Cell Epitopes Induce Distinct Protective and Therapeutic Antitumor Responses in HER-2 Transgenic Mice" The Journal of Immunology, 2003, 171:1588-1595.
Rovero et al., "DNA Vaccination Against Rat Her-2/Neu p185 More Effectively Inhibits Carcinogenesis Than Transplantable Carcinomas in Transgenic BALB/c Mice" The Journal of Immunology, 2000, 165:5133-5142.
Sato et al., "Combination Docetaxel and Trastuzumab Treatment for Patients with HER-2-Overexpressing Metastatic Breast Cancer: A Multicenter, Phase-II Study" Breast Cancer, 2006, 13:166-171.
Triozzi et al., "Effect of Docetaxel Chemotherapy on the Activity of a Gonadotropin Releasing Hormone vaccine in Patients With Advanced Prostate Cancer" The Prostate, 2005, 65:316-321.
Yu et al., "Effective Combination of Chemotherapy and Dendritic Cell Administration for the Treatment of Advanced-Stage Experimental Breast Cancer" Clinical Cancer Research, 2003, 9:285-294.
Carroll et al., Highly Attenuated Modified Vaccinia Virus Ankara (MVA) as an Effective Recombinant Vector: a Murine Tumor Model. Vaccine, vol. 15, No. 4, pp. 387-394 (1997).
Burris et al., Doxetaxel (Taxotere) in HER-2-positive patients and in combination with Trastuzumab (Herceptin), Sem. in Oncology, 2000, 27:19-23.
Kastenmuller et al., Infection of human dendritic cells with recombinant vaccinia virus MVA reveals general persistence of early transcription but distinct maturation-dependent cytopathogenicity, Virology, 2006, 350:276-288.
Mandl et al., MVA-BN-HER2: A novel vaccine for the treatment of breast cancers which overexpress HER-2, Journal of Immunotherapy, 2006, 29:652.
Merck Manuals Online Medical Library, Paclitaxel, Jan. 2009.
Merck Manuals Online Medical Library, Trastuzumab, Jan. 2009.
Merck Manuals Online Medical Library, Docetaxel, Jan. 2009.

* cited by examiner

*Primary Examiner* — Deborah Crouch
(74) *Attorney, Agent, or Firm* — Salvatore J. Arrigo; David C. Hoffman

(57) ABSTRACT

The invention relates to compositions, kits, and methods for cancer therapy using recombinant MVA viruses encoding a tumor-associated antigen, such as HER-2, particularly in combination with taxanes. The taxanes can be administered prior to, at the same time as, or after the recombinant MVA virus.

56 Claims, 10 Drawing Sheets

A

B

A

B

A

B

C

METHODS FOR TREATING CANCER WITH A RECOMBINANT MVA EXPRESSING HER-2

CROSS REFERENCE TO RELATED APPLICATIONS

This application is a continuation of U.S. application Ser. No. 11/905,876, filed Oct. 5, 2007, and issued Oct. 5, 2010, as U.S. Pat. No. 7,807,146, which claims the benefit of U.S. Provisional Application No. 60/850,031, filed on Oct. 6, 2006, both of which are hereby incorporated herein by reference.

FIELD OF THE INVENTION

The invention relates to the treatment of cancers using MVA viruses encoding a tumor-associated antigen, particularly in combination with taxanes.

BACKGROUND OF THE INVENTION

Modified Vaccinia Ankara (MVA) virus is related to vaccinia virus, a member of the genera Orthopoxvirus, in the family of Poxyiridae. MVA was generated by 516 serial passages on chicken embryo fibroblasts of the Ankara strain of vaccinia virus (CVA) (for review see Mayr, A., et al. Infection 3, 6-14 (1975)). As a consequence of these long-term passages, the genome of the resulting MVA virus had about 31 kilobases of its genomic sequence deleted and, therefore, was described as highly host cell restricted for replication to avian cells (Meyer, H. et al., J. Gen. Virol. 72, 1031-1038 (1991)). It was shown in a variety of animal models that the resulting MVA was significantly avirulent (Mayr, A. & Danner, K., Dev. Biol. Stand. 41: 225-34 (1978)). Additionally, this MVA strain has been tested in clinical trials as a vaccine to immunize against the human smallpox disease (Mayr et al., Zbl. Bakt. Hyg. I, Abt. Org. B 167, 375-390 (1987); Stickl et al., Dtsch. med. Wschr. 99, 2386-2392 (1974)). These studies involved over 120,000 humans, including high-risk patients, and proved that, compared to vaccinia-based vaccines, MVA had diminished virulence or infectiousness, while it induced a good specific immune response.

In the following decades, MVA was engineered for use as a viral vector for recombinant gene expression or as a recombinant vaccine (Sutter, G. et al., Vaccine 12: 1032-40 (1994)).

Even though Mayr et al. demonstrated during the 1970s that MVA is highly attenuated and avirulent in humans and mammals, certain investigators have reported that MVA is not fully attenuated in mammalian and human cell lines since residual replication might occur in these cells. (Blanchard et al., J Gen Viol 79, 1159-1167 (1998); Carroll & Moss, Virology 238, 198-211 (1997); Altenberger, U.S. Pat. No. 5,185, 146; Ambrosini et al., J Neurosci Res 55(5), 569 (1999)). It is assumed that the results reported in these publications have been obtained with various known strains of MVA, since the viruses used essentially differ in their properties, particularly in their growth behavior in various cell lines. Such residual replication is undesirable for various reasons, including safety concerns in connection with use in humans.

Strains of MVA having enhanced safety profiles for the development of safer products, such as vaccines or pharmaceuticals, have been described. See U.S. Pat. Nos. 6,761,893 and 6,193,752. Such strains are capable of reproductive replication in non-human cells and cell lines, especially in chicken embryo fibroblasts (CEF), but are not capable of significant reproductive replication in certain human cell lines known to permit replication with known vaccinia strains. Such cell lines include a human keratinocyte cell line, HaCat (Boukamp et al. J Cell Biol 106(3): 761-71 (1988)), a human cervix adenocarcinoma cell line, HeLa (ATCC No. CCL-2), a human embryo kidney cell line, 293 (ECACC No. 85120602), and a human bone osteosarcoma cell line, 143B (ECACC No. 91112502). Such strains are also not capable of significant reproductive replication in vivo, for example, in certain mouse strains, such as the transgenic mouse model AGR 129, which is severely immune-compromised and highly susceptible to a replicating virus. See U.S. Pat. No. 6,761,893. One such MVA strain and its derivatives and recombinants, referred to as "MVA-BN," have been described. See U.S. Pat. Nos. 6,761,893 and 6,193,752.

MVA and MVA-BN have each been engineered for use as a viral vector for recombinant gene expression or as a recombinant vaccine. See, e.g., Sutter, G. et al., Vaccine 12: 1032-40 (1994), U.S. Pat. Nos. 6,761,893 and 6,193,752.

Certain approaches to cancer immunotherapy have included vaccination with tumor-associated antigens. In certain instances, such approaches have included use of a delivery system to promote host immune responses to tumor-associated antigens. In certain instances, such delivery systems have included recombinant viral vectors. See, e.g., Harrop et al., Front. Biosci. 11:804-817 (2006); Arlen et al., Semin. Oncol. 32:549-555 (2005); Liu et al., Proc. Natl. Acad. Sci. USA 101 (suppl. 2):14567-14571 (2004).

HER-2 is a tumor-associated antigen that is over-expressed in tumor cells of a number of cancer patients. Immunization with various HER-2 polypeptides has been used to generate an immune response against tumor cells expressing this antigen. See, e.g., Renard et al., J. Immunology 171:1588-1595 (2003); Mittendorf et al., Cancer 106:2309-2317 (2006).

Taxanes, such as paclitaxel and docetaxel, have been used as chemotherapies for cancer patients. Chemotherapy with taxanes has been combined with different tumor vaccine treatments, resulting in a variety of results. See, Chu et al., J. Immunotherapy 29: 367-380 (2006); Machiels et al., Cancer Res. 61: 3689-3697 (2001); Prell et al., Cancer Immunol. Immunother. 55: 1285-1293 (2006); Arlen et al., Clinical Breast Cancer 7: 176-179 (2006); and Arlen et al., Clinical Cancer Res. 12: 1260-1269 (2006). The combination of cancer vaccines with chemotherapies has been reviewed in Chong et al., Expert Opin. Phamacother. 6: 1-8 (2005) and Emens et al., Endocrine-Related Cancer 12: 1-17 (2005).

Based on the above, a need in the art exists for reagents and methods for cancer therapy.

BRIEF SUMMARY OF THE INVENTION

The invention encompasses methods for treating cancer patients. In one embodiment, the method comprises administering to the patient a recombinant MVA encoding a polypeptide comprising a HER-2 antigen and administering to the patient a tumoricidal dose of a taxane. The combination treatment is superior to either treatment alone.

In a preferred embodiment, the MVA is MVA-BN.

In one embodiment, the HER-2 antigen comprises SEQ ID NO:2.

The recombinant MVA can be administered prior to the tumoricidal dose of the taxane, at the same time as the tumoricidal dose of the taxane, or after the tumoricidal dose of the taxane.

In a preferred embodiment, the taxane is docetaxel. In another preferred embodiment, the taxane is paclitaxel. In one embodiment, the taxane is docetaxel at a dose of 75-100 mg/m$^2$. In one embodiment, the taxane is paclitaxel at a dose of 135-175 mg/m$^2$.

In one embodiment, the recombinant MVA is administered 1-26 weeks prior to the tumoricidal dose of the taxane. In one embodiment, the recombinant MVA is administered 1-3 weeks prior to the tumoricidal dose of the taxane.

In one embodiment, the recombinant MVA is administered 2-60 days after the tumoricidal dose of the taxane. In one embodiment, the recombinant MVA is administered 2-7 days after the tumoricidal dose of the taxane.

The invention further encompasses a kit for treating a cancer patient containing a recombinant MVA encoding a polypeptide comprising a HER-2 antigen and instructions to administer the recombinant MVA prior to the tumoricidal dose of the taxane, at the same time as the tumoricidal dose of the taxane, or after the tumoricidal dose of the taxane.

The invention further encompasses a recombinant vaccinia virus encoding a polypeptide comprising a HER-2 antigen, wherein the HER-2 antigen comprises SEQ ID NO:2.

DETAILED DESCRIPTION OF CERTAIN EMBODIMENTS

Figure 1:
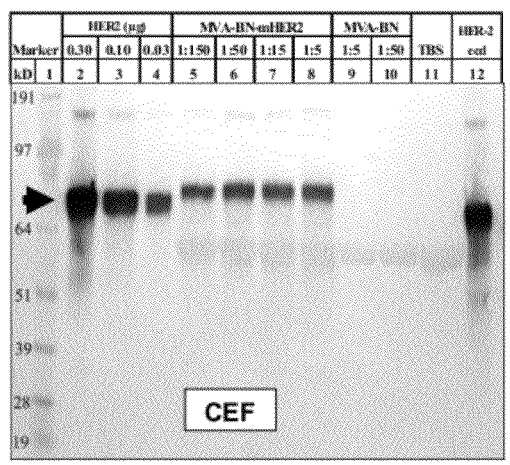
FIG. 1A-B. Western blot analysis of mHER2 expression in primary CEF cells (A) or HeLa cells (B) following inoculation with MVA-BN-mHER2. Cell cultures were inoculated with MVA-BN or MVA-BN-mHER2 at the dilutions shown, or with TBS buffer, as described in Example 1. Cells were harvested from the cultures 24 hours later and cell lysates were prepared. Samples were electrophoresed through SDS-PAGE gels and electroblotted onto nitrocellulose membranes. mHER2 protein was detected by incubating with rabbit anti-HER-2 antiserum followed by detection with alkaline phosphatase-labeled anti-rabbit antibody and a chromogenic substrate as described in Example 1. Full length HER-2 protein and the extracellular domain of HER-2 are shown for reference. The arrows mark the position of protein detected with anti-HER-2 antiserum in lysates from cell cultures.
Figure 1:
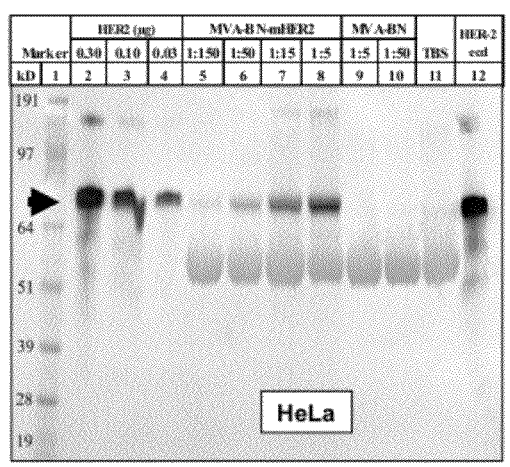

In one embodiment, the invention encompasses the use of recombinant MVA viruses for cancer therapy. The recombinant MVAs are generated by insertion of heterologous sequences into an MVA virus. Examples of MVA virus strains that are useful in the practice of the present invention and that have been deposited in compliance with the requirements of the Budapest Treaty are strains MVA 572, deposited at the European Collection of Animal Cell Cultures (ECACC), Vaccine Research and Production Laboratory, Public Health Laboratory Service, Centre for Applied Microbiology and Research, Porton Down, Salisbury, Wiltshire SP4 0JG, United Kingdom, with the deposition number ECACC 94012707 on Jan. 27, 1994, and MVA 575, deposited at the European Collection of Cell Cultures (ECACC) under deposition number ECACC 00120707 on Dec. 7, 2000. MVA-BN, deposited on Aug. 30, 2000 at the European Collection of Cell Cultures (ECACC) under deposition number V00083008, and its derivatives, are additional exemplary strains.

Although MVA-BN is preferred for its higher safety (less replication competent), all MVAs are suitable for this invention. According to an embodiment of the present invention, the MVA strain is MVA-BN and its derivatives. A definition of MVA-BN and its derivatives is given in PCT/EP01/13628.

In certain embodiments, an MVA comprises at least one tumor-associated antigen. In a preferred embodiment, the tumor-associated antigen is a HER-2 antigen. In one embodiment, the HER-2 antigen comprises the sequence of SEQ ID NO:2.

In further embodiments, the tumor-associated antigen is modified to include one or more foreign $T_H$ epitopes. Such a cancer immunotherapeutic agent is described herein in a non-limiting example and is referred to as "MVA-BN-mHER2." As described herein, such cancer immunotherapeutic agents, including, but not limited to MVA-BN-mHER2, are useful for the treatment of cancer. The invention allows for the use of such agents in prime/boost vaccination regimens of humans and other mammals, including immunocompromised patients; and inducing both humoral and cellular immune responses, such as inducing a Th1 immune response in a pre-existing Th2 environment.

The term "polypeptide" refers to a polymer of two or more amino acids joined to each other by peptide bonds or modified peptide bonds. The amino acids may be naturally occurring as well as non-naturally occurring, or a chemical analogue of a naturally occurring amino acid. The term also refers to proteins, i.e. functional biomolecules comprising at least one polypeptide; when comprising at least two polypeptides, these may form complexes, be covalently linked, or may be non-covalently linked. The polypeptide(s) in a protein can be glycosylated and/or lipidated and/or comprise prosthetic groups.

In certain embodiments, the MVA is MVA-BN, deposited on Aug. 30, 2000, at the European Collection of Cell Cultures (ECACC) under number V00083008, and described in U.S. Pat. Nos. 6,761,893 and 6,193,752. As described in those patent publications, MVA-BN does not reproductively replicate in cell lines 293, 143B, HeLa and HaCat. In particular, MVA-BN exhibits an amplification ratio of 0.05 to 0.2 in the human embryo kidney cell line 293. In the human bone osteosarcoma cell line 143B, MVA-BN exhibits an amplification ratio of 0.0 to 0.6. MVA-BN exhibits an amplification ratio of 0.04 to 0.8 in the human cervix adenocarcinoma cell line HeLa, and 0.02 to 0.8 in the human keratinocyte cell line HaCat. MVA-BN has an amplification ratio of 0.01 to 0.06 in African green monkey kidney cells (CV1: ATCC No. CCL-70).

The amplification ratio of MVA-BN is above 1 in chicken embryo fibroblasts (CEF: primary cultures) as described in U.S. Pat. Nos. 6,761,893 and 6,193,752. The virus can be easily propagated and amplified in CEF primary cultures with a ratio above 500.

In certain embodiments, a recombinant MVA is a derivative of MVA-BN. Such "derivatives" include viruses exhibiting essentially the same replication characteristics as the deposited strain (ECACC No. V00083008), but exhibiting differences in one or more parts of its genome. Viruses having the same "replication characteristics" as the deposited virus are viruses that replicate with similar amplification ratios as the deposited strain in CEF cells and the cell lines, HeLa, HaCat and 143B; and that show similar replication characteristics in vivo, as determined, for example, in the AGR129 transgenic mouse model.

In certain embodiments, the MVA is a recombinant vaccinia virus that contains additional nucleotide sequences that are heterologous to the vaccinia virus. In certain such embodiments, the heterologous sequences code for epitopes that induce a response by the immune system. Thus, in certain embodiments, the recombinant MVA is used to vaccinate against the proteins or agents comprising the epitope. In a preferred embodiment, the epitope is a tumor-associated antigen, preferably, HER-2. In one embodiment, the HER-2 antigen comprises the sequence of SEQ ID NO:2.

In certain embodiments, a heterologous nucleic acid sequence is inserted into a non-essential region of the virus genome. In certain of those embodiments, the heterologous nucleic acid sequence is inserted at a naturally occurring deletion site of the MVA genome as described in PCT/EP96/02926. Methods for inserting heterologous sequences into the poxviral genome are known to a person skilled in the art.

In certain embodiments, pharmaceutical compositions comprise one or more pharmaceutically acceptable and/or approved carriers, additives, antibiotics, preservatives, adjuvants, diluents and/or stabilizers. Such additives include, for example, but not limited to, water, saline, glycerol, ethanol, wetting or emulsifying agents, and pH buffering substances. Exemplary carriers are typically large, slowly metabolized molecules such as proteins, polysaccharides, polylactic acids, polyglycolic acids, polymeric amino acids, amino acid copolymers, lipid aggregates, or the like.

For the preparation of vaccines, the MVA can be converted into a physiologically acceptable form. In certain embodiments, such preparation is based on experience in the preparation of poxvirus vaccines used for vaccination against smallpox, as described, for example, in Stickl, H. et al., Dtsch. med. Wschr. 99, 2386-2392 (1974).

An exemplary preparation follows. Purified virus is stored at −80° C. with a titer of $5 \times 10^8$ TCID$_{50}$/ml formulated in 10 mM Tris, 140 mM NaCl, pH 7.4. For the preparation of vaccine shots, e.g., $10^2$-$10^8$ particles of the virus can be lyophilized in phosphate-buffered saline (PBS) in the presence of 2% peptone and 1% human albumin in an ampoule, preferably a glass ampoule. Alternatively, the vaccine shots can be prepared by stepwise, freeze-drying of the virus in a formulation. In certain embodiments, the formulation contains additional additives such as mannitol, dextran, sugar, glycine, lactose, polyvinylpyrrolidone, or other additives, such as, including, but not limited to, antioxidants or inert gas, stabilizers or recombinant proteins (e.g. human serum albumin) suitable for in vivo administration. The ampoule is then sealed and can be stored at a suitable temperature, for example, between 4° C. and room temperature for several months. However, as long as no need exists, the ampoule is stored preferably at temperatures below −20° C.

In various embodiments involving vaccination or therapy, the lyophilisate is dissolved in 0.1 to 0.5 ml of an aqueous solution, preferably physiological saline or Tris buffer, and administered either systemically or locally, i.e., by parenteral, subcutaneous, intravenous, intramuscular, intranasal, intradermal, or any other path of administration known to a skilled practitioner. Optimization of the mode of administration, dose, and number of administrations is within the skill and knowledge of one skilled in the art.

In certain embodiments, attenuated vaccinia virus strains are useful to induce immune responses in immune-compromised animals, e.g., monkeys (CD4<400/µl of blood) infected with SIV, or immune-compromised humans. The term "immune-compromised" describes the status of the immune system of an individual that exhibits only incomplete immune responses or has a reduced efficiency in the defense against infectious agents.

Certain Exemplary Tumor-Associated Antigens

In certain embodiments, an immune response is produced in a subject against a cell-associated polypeptide antigen. In certain such embodiments, a cell-associated polypeptide antigen is a tumor-associated antigen.

In certain embodiments, a cell-associated polypeptide antigen is a self-protein antigen other than a tumor-associated antigen, which is related to various pathological processes, or a viral antigen, or antigens derived from an intracellular parasite or bacterium. In certain instances, such pathogen-associated antigens are often relatively poor immunogens (e.g. antigens from mycobacteria such as *Mycobacterium tuberculosis* and *Mycobacterium leprae*, but also from protozoans such as *Plasmodium* spp.).

Numerous tumor-associated antigens are known in the art. Exemplary tumor-associated antigens include, but are not limited to, 5 alpha reductase, alpha-fetoprotein, AM-1, APC, April, BAGE, beta-catenin, Bcl12, bcr-abl, CA-125, CASP-8/FLICE, Cathepsins, CD19, CD20, CD21, CD23, CD22, CD33 CD35, CD44, CD45, CD46, CD5, CD52, CD55, CD59, CDC27, CDK4, CEA, c-myc, Cox-2, DCC, DcR3, E6/E7, CGFR, EMBP, Dna78, farnesyl transferase, FGF8b, FGF8a, FLK-1/KDR, folic acid receptor, G250, GAGE-family, gastrin 17, gastrin-releasing hormone, GD2/GD3/GM2, GnRH, GnTV, GP1, gp100/Pmel17, gp-100-in4, gp15, gp75/TRP-1, hCG, heparanse, Her2/neu, HMTV, Hsp70, hTERT, IGFR1, IL-13R, iNOS, Ki67, KIAA0205, K-ras, H-ras, N-ras, KSA, LKLR-FUT, MAGE-family, mammaglobin, MAP17, melan-A/MART-1, mesothelin, MIC A/B, MT-MMPs, mucin, NY-ESO-1, osteonectin, p15, P170/MDR1, p53, p97/melanotransferrin, PAI-1, PDGF, uPA, PRAME, probasin, progenipoientin, PSA, PSM, RAGE-1, Rb, RCAS1, SART-1, SSX-family, STAT3, STn, TAG-72, TGF-alpha, TGF-beta, Thymosin-beta-15, TNF-alpha, TP1, TRP-2, tyrosinase, VEGF, ZAG, p16INK4, and glutathione-S-transferase.

One exemplary tumor-associated antigen is HER-2. HER-2 is a member of the epidermal growth factor receptor family (c-erbB) which consists of four different receptors to date: c-erbB-1 (EGFr), c-erbB-2 (HER-2, c-Neu), c-erbB-3 and c-erbB-4 (Salomon et al, 1995). C-erbB-3 and c-erbB-4 are less well characterized than EGFr and HER-2. HER-2 is an integral membrane glycoprotein. The mature protein has a molecular weight of 185 kD with structural features that closely resemble the EGFr receptor (Prigent et al, 1992). EGFr is also an integral membrane receptor consisting of one subunit. It has an apparent molecular weight of 170 kD and consists of a surface ligand-binding domain of 621 amino acids, a single hydrophobic transmembrane domain of 23 amino acids, and a highly conserved cytoplasmic tyrosine kinase domain of 542 amino acids. The protein is N-glycosylated (Prigent et al, 1994).

All proteins in this family are tyrosine kinases. Interaction with the ligand leads to receptor dimerization, which increases the catalytic action of the tyrosine kinase (Bernard. 1995, Chantry 1995). The proteins within the family are able to homo- and heterodimerise, which is important for their activity. The EGFr conveys growth promoting effects and stimulates uptake of glucose and amino acids by cells (Prigent et al 1992). HER-2 also conveys growth promoting signals.

The epidermal growth factor receptor is expressed on normal tissues in low amounts, but it is overexpressed in many types of cancers. EGFr is overexpressed in breast cancers (Earp et al, 1993, Eppenberger 1994), gliomas (Schlegel et al, 1994), gastric cancer (Tkunaga et al, 1995), cutaneous squamous carcinoma (Fujii 1995), ovarian cancer (van Dam et al, 1994) and others. HER-2 is also expressed on few normal human tissues in low amount, most characteristically on secretory epithelia. Over-expression of HER-2 occurs in about 30% of breast, gastric, pancreatic, bladder and ovarian cancers.

The expression of these receptors varies depending on the degree of differentiation of the tumors and the cancer type, e.g., in breast cancer, primary tumors overexpress both receptors; whereas in gastric cancer, the overexpression occurs at a later stage in metastatic tumours (Salomon et al, 1995). The number of overexpressed receptors on carcinoma cells is greater than $10^6$/cell for several head and neck cancers, vulva, breast and ovarian cancer lines isolated from patients (Dean et al, 1994).

There are several reasons why the EGFr family of receptors constitutes suitable targets for tumor immunotherapy. First, they are overexpressed in many types of cancers, which should direct the immune response towards the tumor. Second, the tumors often express or overexpress the ligands for this family of receptors and some are hypersensitive to the proliferative effects mediated by the ligands. Third, patients with tumors that overexpress growth factor receptors often have a poor prognosis. The overexpression has been closely linked with poor prognosis especially in breast cancer, lung cancer, and bladder cancer and can be associated with invasive/metastatic phenotypes, which are rather insensitive to conventional therapies (Eccles et al, 1994).

Modified Tumor-Associated Antigens

In certain embodiments, a cell-associated polypeptide antigen is modified such that a CTL response is induced against a cell which presents epitopes derived from a polypeptide antigen on its surface, when presented in association with an MHC Class I molecule on the surface of an APC. In certain such embodiments, at least one first foreign $T_H$ epitope, when presented, is associated with an MHC Class II molecule on the surface of the APC. In certain such embodiments, a cell-associated antigen is a tumor-associated antigen.

Exemplary APCs capable of presenting epitopes include dendritic cells and macrophages. Additional exemplary APCs include any pino- or phagocytizing APC, which is capable of simultaneously presenting 1) CTL epitopes bound to MHC class I molecules and 2) $T_H$ epitopes bound to MHC class II molecules.

In certain embodiments, modifications to HER-2 are made such that, after administration to a subject, polyclonal antibodies are elicited that predominantly react with HER-2. Such antibodies could attack and eliminate tumor cells as well as prevent metastatic cells from developing into metastases. The effector mechanism of this anti-tumor effect would be mediated via complement and antibody dependent cellular cytotoxicity. In addition, the induced antibodies could also inhibit cancer cell growth through inhibition of growth factor dependent oligo-dimerisation and internalisation of the receptors. In certain embodiments, such modified HER-2 polypeptide antigens could induce CTL responses directed against known and/or predicted HER-2 epitopes displayed by the tumor cells.

In certain embodiments, a modified HER-2 polypeptide antigen comprises a CTL epitope of the cell-associated polypeptide antigen and a variation, wherein the variation comprises at least one CTL epitope of a foreign $T_H$ epitope. Certain such modified HER-2 polypeptide antigens comprising at least one CTL epitope and a variation comprising at least one CTL epitope of a foreign $T_H$ epitope, and methods of producing the same, are described in U.S. Pat. No. 7,005,498 and U.S. Patent Pub. Nos. 2004/0141958 and 2006/0008465.

In certain embodiments, a foreign $T_H$ epitope is a naturally-occurring "promiscuous" T-cell epitope. Such promiscuous T-cell epitopes are active in a large proportion of individuals of an animal species or an animal population. In certain embodiments, a vaccine comprises such promiscuous T-cell epitopes. In certain such embodiments, use of promiscuous T-cell epitopes reduces the need for a very large number of different CTL epitopes in the same vaccine. Exemplary promiscuous T-cell epitopes include, but are not limited to, epitopes from tetanus toxin, including but not limited to, the P2 and P30 epitopes (Panina-Bordignon et al., 1989), diphtheria toxin, Influenza virus hemagluttinin (HA), and P. falciparum CS antigen.

Additional promiscuous T-cell epitopes include peptides capable of binding a large proportion of HLA-DR molecules encoded by the different HLA-DR. See, e.g., WO 98/23635 (Frazer I H et al., assigned to The University of Queensland); Southwood S et. al, 1998, J. Immunol. 160: 3363 3373; Sinigaglia F et al., 1988, Nature 336: 778 780; Rammensee H G et al., 1995, Immunogenetics 41: 4 178 228; Chicz R M et al., 1993, J. Exp. Med. 178: 27 47; Hammer J et al., 1993, Cell 74: 197 203; and Falk K et al., 1994, Immunogenetics 39: 230 242. The latter reference also deals with HLA-DQ and -DP ligands. All epitopes listed in these references are relevant as candidate natural epitopes as described herein, as are epitopes which share common motifs with these.

In certain other embodiments, the promiscuous T-cell epitope is an artificial T-cell epitope which is capable of binding a large proportion of haplotypes. In certain such embodiments, the artificial T-cell epitope is a pan DR epitope peptide ("PADRE") as described in WO 95/07707 and in the corresponding paper Alexander J et al., 1994, Immunity 1: 751 761.

mHER2

Various modified HER-2 polypeptide antigens and methods for producing the same are described in U.S. Pat. No. 7,005,498 and U.S. Patent Pub. Nos. 2004/0141958 and 2006/0008465, which are hereby incorporated by reference. Those documents describe various modified HER-2 polypeptide antigens comprising promiscuous T-cell epitopes at different positions in the HER-2 polypeptide.

The human HER-2 sequence can be divided into a number of domains based solely on the primary structure of the protein. Those domains are as follows. The extracellular (receptor) domain extends from amino acids 1-654 and contains several subdomains as follows: Domain I (N-terminal domain of mature polypeptide) extends from amino acids 1-173; Domain II (Cysteine rich domain, 24 cysteine residues) extends from amino acids 174-323; Domain III (ligand binding domain in the homologous EGF receptor) extends from amino acids 324-483; and Domain IV (Cysteine rich domain, 20 cysteine residues) extends from amino acids 484-623. The transmembrane residues extend from amino acids 654-675. The intracellular (Kinase) domain extends from amino acids 655-1235 and contains the tyrosine kinase domain, which extends from amino acids 655-1010 (core TK domain extends from 725-992); and the C-terminal domain, which extends from amino acids 1011-1235.

Selection of sites in the amino acid sequence of HER-2 to be displaced by either the P2 or P30 human T helper epitopes is described in U.S. Pat. No. 7,005,498 and U.S. Patent Pub. Nos. 2004/0141958 and 2006/0008465. To summarize, the following parameters were considered:
 1. Known and predicted CTL epitopes;
 2. Homology to related receptors (EGFR in particular);
 3. Conservation of cysteine residues;
 4. Predicted loop, α-helix and β-sheet structures;
 5. Potential N-glycosylation sites;
 6. Prediction of exposed and buried amino acid residues;
 7. Domain organization.

The CTL epitopes appear to be clustered in domain I, domain III, the TM domain and in two or three "hot spots" in the TK domain. As described in U.S. Pat. No. 7,005,498 and U.S. Patent Pub. Nos. 2004/0141958 and 2006/0008465, these should be largely conserved.

Regions with a high degree of homology with other receptors are likely to be structurally important for the "overall" tertiary structure of HER-2, and hence for antibody recognition, whereas regions with low homology possibly can be exchanged with only local alterations of the structure as the consequence.

Cysteine residues are often involved in intramolecular disulphide bridge formation and are thus involved in the tertiary structure and should not be changed. Regions predicted to form alpha-helix or beta-sheet structures should be avoided as insertion points of foreign epitopes, as these regions are thought to be involved in folding of the protein.

Potential N-glycosylation sites should be conserved if mannosylation of the protein is desired.

Regions predicted (by their hydrophobic properties) to be interior in the molecule preferably should be conserved as these could be involved in the folding. In contrast, solvent exposed regions could serve as candidate positions for insertion of the model $T_H$ epitopes P2 and P30.

Finally, the domain organization of the protein should be taken into consideration because of its relevance for protein structure and function.

As described in U.S. Pat. No. 7,005,498 and U.S. Patent Pub. Nos. 2004/0141958 and 2006/0008465, the focus of the strategy has been to conserve the structure of the extracellular part of HER-2 as much as possible, because this is the part of the protein which is relevant as a target for neutralizing antibodies. By contrast, the intracellular part of native membrane bound HER-2 on the surface of cancer cells is inaccessible for the humoral immune system.

Various exemplary constructs using the P2 and P30 epitopes of tetanus toxin inserted in various domains of HER-2 are provided in U.S. Pat. No. 7,005,498 and U.S. Patent Pub. Nos. 2004/0141958 and 2006/0008465. One exemplary modified HER-2 polypeptide antigen, referred to as "mHER2," comprises the extracellular domains and nine amino acids of the transmembrane domain; the P2 epitope inserted in Domain II between amino acid residues 273 to 287 of the modified HER-2 polypeptide; and the P30 epitope inserted in Domain IV between amino acid residues 655 to 675 of the modified HER-2 polypeptide.

Recombinant MVA-BN-mHER2

In a non-limiting embodiment, recombinant MVA comprising a tumor-associated antigen, e.g., MVA-BN-mHER2, is constructed as follows. The initial virus stock is generated by recombination in cell culture using a cell type permissive for replication, e.g., CEF cells. Cells are both inoculated with an attenuated vaccinia virus, e.g., MVA-BN, and transfected with a recombination plasmid (e.g., pBN146) that encodes the tumor-associated antigen, e.g., mHER2, sequence and flanking regions of the virus genome. In one non-limiting embodiment, the plasmid pBN146 contains sequences which are also present in MVA-BN (the 14L and 15L open reading frames). The mHER2 sequence is inserted between the MVA-BN sequences to allow for recombination into the MVA-BN viral genome. In certain embodiments, the plasmid also contains a selection cassette comprising one or more selection genes to allow for selection of recombinant constructs in CEF cells. In a preferred embodiment, the recombinant MVA encodes a polypeptide comprising SEQ ID NO:2.

Simultaneous infection and transfection of cultures allows homologous recombination to occur between the viral genome and the recombination plasmid. Insert-carrying virus is then isolated, characterized, and virus stocks prepared. In certain embodiments, virus is passaged in CEF cell cultures in the absence of selection to allow for loss of the region encoding the selection genes, gpt and EGFP.

Combination Therapy with Cytotoxic Agents

Cytotoxic agents display immunomodulatory activities at sub-tumoricidal doses that could be beneficial for vaccine efficacy. However, at tumoricidal doses (high doses), these agents could be detrimental to vaccine activities. It has now been demonstrated that human-equivalent tumoricidal doses of docetaxel given to mice during the course of MVA-BN-mHER2 treatment did not affect the vaccine-induced anti-HER-2 antibody titers. Moreover, treatment of mice with MVA-BN-mHER2 increased tumor sensitivity to docetaxel in vivo. Hence, concurrent, prior, or subsequent chemotherapy to MVA-BN-mHER2 treatment can be superior to either treatment alone.

Patients with a cancer mediated by cells over-expressing the tumor-associated antigen HER-2 can be treated by the combination of MVA encoding a HER-2 antigen with a taxane. In a preferred embodiment, the MVA is MVA-BN. In a particularly preferred embodiment, the MVA encodes a polypeptide comprising SEQ ID NO:2.

The recombinant MVA encoding a HER-2 antigen can be administered either systemically or locally, i.e., by parenteral, subcutaneous, intravenous, intramuscular, intranasal, intradermal, or any other path of administration known to a skilled practitioner. In one embodiment, $10^5$-$10^{10}$ TCID$_{50}$ of the recombinant MVA are administered to the patient. Preferably, $10^7$-$10^{10}$ TCID$_{50}$ of the recombinant MVA are administered to the patient. More preferably, $10^8$-$10^{10}$ TCID$_{50}$ of the recombinant MVA are administered to the patient. Most preferably, $10^8$-$10^9$ TCID$_{50}$ of the recombinant MVA are administered to the patient.

The cancer is preferably a breast cancer, a lung cancer, a gastric cancer, a pancreatic cancer, a bladder cancer, or an ovarian cancer. In a preferred embodiment, the cancer is a metastatic breast cancer.

The cancer patient can be any mammal, including a mouse or rat. Preferably, the cancer patient is a primate, most preferably, a human.

In one embodiment, the taxane is docetaxel. In another embodiment, the taxane is paclitaxel. The taxane is preferably administered at a tumoricidal dose. A "tumoricidal dose" of docetaxel is at least 50 mg/m$^2$. Preferably, the tumoricidal dose of docetaxel is 75-100 mg/m$^2$, which corresponds to a dosage of approximately 25-33 mg/kg. A "tumoricidal dose" of paclitaxel is at least 90 mg/m$^2$. Preferably, the tumoricidal dose of paclitaxel is 135-175 mg/m$^2$. A "sub-tumoricidal dose" of a taxane is a dosage below the tumoricidal dosage. The taxane can be administered by an means known to the skilled artisan, for example, intravenously.

In one embodiment, the taxane and the MVA encoding a polypeptide comprising a HER-2 antigen are administered at the same time. The combination treatment is superior to either treatment alone.

In one embodiment, the taxane is administered prior to the MVA encoding a polypeptide comprising a HER-2 antigen. In one embodiment, the MVA encoding a HER-2 antigen is administered within 6 months. In certain embodiments, the MVA encoding a HER-2 antigen is administered within 3 months, within 2 months, or within 1 month after the taxane. In one embodiment, the MVA encoding a HER-2 antigen is administered within 21 days after the taxane. In one embodiment, the MVA encoding a HER-2 antigen is administered within 14 days after the taxane. In one embodiment, the MVA encoding a HER-2 antigen is administered within 7 days after the taxane. Usually, the MVA encoding a HER-2 antigen is administered at least 2 days after treatment with the taxane. The combination treatment is superior to either treatment alone.

In one embodiment, the taxane is administered after the MVA encoding a polypeptide comprising a HER-2 antigen. Usually, the MVA encoding a HER-2 antigen is administered at least 1 week prior to treatment with the taxane. In one embodiment, the MVA encoding a HER-2 antigen is administered less than 2 years prior to the taxane. In certain embodiments, the MVA encoding a HER-2 antigen is administered less than 1 year, less than 6 months, or less than 3 months prior to the taxane. In one embodiment, the MVA encoding a HER-2 antigen is administered 1-26 weeks prior to the taxane. In one embodiment, the MVA encoding a HER-2 antigen is administered 1-9 weeks prior to the taxane. In one embodiment, the MVA encoding a HER-2 antigen is administered 1-3 weeks prior to the taxane. The combination treatment is superior to either treatment alone.

In certain embodiments, the taxane is administered both prior to and after the MVA encoding a HER-2 antigen. In other embodiments, the MVA encoding a HER-2 antigen is administered both prior to and after the taxane. The administration of the MVA and the taxane can be a single administration or multiple administrations. For example, the administrations can be 1, 2, 3, 4, 5, or 6 weeks apart.

The invention encompasses kits comprising recombinant MVA. The recombinant MVA may be contained in a vial or container. Preferably, the recombinant MVA encodes a polypeptide comprising a HER-2 antigen. In various embodiments, kits for vaccination comprising a recombinant MVA for the first vaccination ("priming") in a first vial or container and for a second vaccination ("boosting") in a second via or container.

In one embodiment, the kit can contain a recombinant MVA and instructions for the administration of the recombinant MVA prior to administration of a tumoricidal dose of a taxane. The instructions can instruct that the MVA is to be administered at any time point between 6 months and 1 week prior to taxane administration. In preferred embodiments, the instructions instruct that the MVA is to be administered at any time point between 3 months and 1 week, six weeks and 1 week, 1 month and 1 week, 3 weeks and 1 week, and 2 weeks and 1 week prior to taxane administration. In one embodiment, the instructions can instruct that the MVA is to be administered at any time point between 1 week and 0 days prior to taxane administration.

The kit can also contain a recombinant MVA and instructions for the administration of the recombinant MVA at the same time as administration of a tumoricidal dose of a taxane.

The kit can also contain a recombinant MVA and instructions for the administration of the recombinant MVA after administration of a tumoricidal dose of a taxane. The instructions can instruct that the MVA is to be administered at any time point between 1 day and 6 months after taxane administration. In preferred embodiments, the instructions instruct that MVA is to be administered at any time point between 2 days and 1 week, 2 days and 2 weeks, 2 days and 3 weeks, 2 days and 1 month, 2 days and 2 months, and 2 days and 3 months, and 2 days and 6 months after taxane administration. In one embodiment, the instructions can instruct that the MVA is to be administered at any time point between 0 and 2 days after taxane administration.

EXAMPLES

Example 1

Construction of MVA-BN-mHER2 and Analysis of Protein Expression in Infected Cells Simultaneous infection and transfection of cultures allowed homologous recombination to occur between the viral genome and the recombination plasmid. Insert-carrying virus was isolated, characterized, and virus stocks were prepared.

Plasmid pBN146 contains sequences which are also present in MVA-BN (the 14L and 15L open reading frames). The mHER2 sequence was inserted between the MVA-BN sequences to allow for recombination into the MVA-BN viral genome. Thus, a plasmid was constructed that contained the mHER2 sequence downstream of a poxvirus promoter, specifically the cowpox virus A-type inclusion body gene promoter. The plasmid also contained a selection cassette comprising a synthetic vaccinia virus promoter (Ps), a drug resistance gene (guanine-xanthine phosphoribosyltransferase; Ecogpt), an internal ribosomal entry site (IRES), and the enhanced green fluorescent protein (EGFP). Both selection genes (gpt and EGFP) were encoded by a single bicistronic transcript.

The HER-2 sequence was modified by addition of nucleotides sequences encoding tetanus toxin epitopes of p2 and p30 to increase the immune response against it. After mHER2 was inserted into the MVA-BN genome, the virus "insert region" had the following structure:

ATI promoter-mHER2 sequence-Ps promoter-gpt-IRES-EGFP. The insert region was flanked by MVA-BN 14L intergenic region sequences (F1 and F2) in the bacterial recombination plasmid pBN146. The nucleotide sequence of the construct is shown below.

(SEQ ID NO: 1)
AGTATGCATTTTTACGGATGGAGTCTCGGTCTAAAAACGGGAATGTACTA

TCTACGTACGAAACCCGCATCCGCTCCCATTCAATTCACATTGGACAAGG

ATAAAATAAAACCACTGGTGGTTTGCGATTCCGAAATCTGTACATCATGC

AGTGGTTAAACAAATCTAGAACTAGTTTAATTAAGGAGCTGTTTTGAATA

AAATTTTTTTATAATAAATCTAGAACTAGTGGATCCCCCGGGCTGCAGGA

ATTCGATCTAGCCGCCACCATGGAGCTGGCGGCCTTGTGCCGCTGGGGGC

TCCTCCTCGCCCTCTTGCCCCCCGGAGCCGCGAGCACCCAAGTGTGCACC

GGCACAGACATGAAGCTGCGGCTCCCTGCCAGTCCCGAGACCCACCTGGA

CATGCTCCGCCACCTCTACCAGGGCTGCCAGGTGGTGCAGGGAAACCTGG

AACTCACCTACCTGCCCACCAATGCCAGCTTAAGTTTCCTGCAGGATATC

CAGGAGGTGCAGGGCTACGTGCTCATCGCTCACAACCAAGTGAGGCAGGT

CCCACTGCAGAGGCTGCGGATTGTGCGAGGCACCCAGCTCTTTGAGGACA

ACTATGCCCTGGCCGTGCTAGACAATGGAGACCCGCTGAACAATACCACC

CCTGTCACAGGGGCCTCCCCAGGAGGCCTGCGGGAGCTGCAGCTTCGAAG

CCTCACAGAGATCTTGAAAGGAGGGGTCTTGATCCAGCGGAACCCCCAGC

TCTGCTACCAGGACACGATTTTGTGGAAGGACATCTTCCACAAGAACAAC

CAGCTGGCTCTCACACTGATAGACACCAACCGCTCTCGGGCCTGCCACCC

CTGTTCTCCGATGTGTAAGGGCTCCCGCTGCTGGGGAGAGAGTTCTGAGG

ATTGTCAGAGCCTGACGCGCACTGTCTGTGCCGGTGGCTGTGCCCGCTGC

AAGGGGCCACTGCCCACTGACTGCTGCCATGAGCAGTGTGCTGCCGGCTG

CACGGGCCCCAAGCACTCTGACTGCCTGGCCTGCCTCCACTTCAACCACA

GTGGCATCTGTGAGCTGCACTGCCCAGCCCTGGTCCAGTACATCAAAGCT

AACTCCAAATTCATCGGTATCACCGAGCTGCGGTATACATTCGGCGCCAG

CTGTGTGACTGCCTGTCCCTACAACTACCTTTCTACGGACGTGGGATCCT

GCACCCTCGTCTGCCCCCTGCACAACCAAGAGGTGACAGCAGAGGATGGA

ACACAGCGGTGTGAGAAGTGCAGCAAGCCCTGTGCCCGAGTGTGCTATGG

TCTGGGCATGGAGCACTTGCGAGAGGTGAGGGCAGTTACCAGTGCCAATA

TCCAGGAGTTTGCTGGCTGCAAGAAGATCTTTGGGAGCCTGGCATTTCTG

CCGGAGAGCTTTGATGGGGACCCAGCCTCCAACACTGCCCCGCTCCAGCC

AGAGCAGCTCCAAGTGTTTGAGACTCTGGAAGAGATCACAGGTTACCTAT

ACATCTCAGCATGGCCGGACAGCCTGCCTGACCTCAGCGTCTTCCAGAAC

CTGCAAGTAATCCGGGGACGAATTCTGCACAATGGCGCCTACTCGCTGAC

CCTGCAAGGGCTGGGCATCAGCTGGCTGGGGCTGCGCTCACTGAGGGAAC

TGGGCAGTGGACTGGCCCTCATCCACCATAACACCCACCTCTGCTTCGTG

CACACGGTGCCCTGGGACCAGCTCTTTCGGAACCCGCACCAAGCTCTGCT

CCACACTGCCAACCGGCCAGAGGACGAGTGTGTGGGCGAGGGCCTGGCCT

-continued
```
GCCACCAGCTGTGCGCCCGAGGGCACTGCTGGGGTCCAGGGCCCACCCAG

TGTGTCAACTGCAGCCAGTTCCTTCGGGGCCAGGAGTGCGTGGAGGAATG

CCGAGTACTGCAGGGGCTCCCCAGGGAGTATGTGAATGCCAGGCACTGTT

TGCCGTGCCACCCTGAGTGTCAGCCCCAGAATGGCTCAGTGACCTGTTTT

GGACCGGAGGCTGACCAGTGTGTGGCCTGTGCCCACTATAAGGACCCTCC

CTTCTGCGTGGCCCGCTGCCCCAGCGGTGTGAAACCTGACCTCTCCTACA

TGCCCATCTGGAAGTTTCCAGATGAGGAGGGCGCATGCCAGCCTTGCCCC

ATCAACTGCACCCACTCCTGTGTGGACCTGGATGACAAGGGCTGCCCCGC

CGAGCAGAGAGCCAGCCCTCTGACGTCCTTCAACAACTTCACCGTGAGCT

TCTGGCTGCGCGTGCCCAAGGTGAGCGCCAGCCACCTGGAGATCGTCTCT

GCGGTGGTTGGCATTCTGTAGAAGCTTGGTACCGAGCTCGGATCCACTAG

TCCAGTGTGGTGGAATTCTGCAGATATCCAGCACAGTGGCGGCCATCAAG

CTTATCGATACCGTCGACCTCGAGGGGGGGCCCGGTACCCAGTTAATTAA

GGATCCCCCGGGCTGCAGGAATTCCATTTTTATTCTCAAATGAGATAAAG

TGAAAATATATATCATATATACAAAGTA.
```

HER2 start and stop codons are indicated in bold. Flanking sequences are indicated in italics.

Translation of the encoded mHER2 polypeptide is shown below:

(SEQ ID NO: 2)
MELAALCRWGLLLALLPPGAASTQVCTGTDMKLRLPASPETHLDMLRHL

YQGCQVVQGNLELTYLPTNASLSFLQDIQEVQGYVLIAHNQVRQVPLQR

LRIVRGTQLFEDNYALAVLDNGDPLNNTTPVTGASPGGLRELQLRSLTE

ILKGGVLIQRNPQLCYQDTILWKDIFHKNNQLALTLIDTNRSRACHPCS

PMCKGSRCWGESSEDCQSLTRTVCAGGCARCKGPLPTDCCHEQCAAGCT

GPKHSDCLACLHFNHSGICELHCPALVQYIKANSKFIGITELRYTFGAS

CVTACPYNYLSTDVGSCTLVCPLHNQEVTAEDGTQRCEKCSKPCARVCY

GLGMEHLREVRAVTSANIQEFAGCKKIFGSLAFLPESFDGDPASNTAPL

QPEQLQVFETLEEITGYLYISAWPDSLPDLSVFQNLQVIRGRILHNGAY

SLTLQGLGISWLGLRSLRELGSGLALIHHNTHLCFVHTVPWDQLFRNPH

QALLHTANRPEDECVGEGLACHQLCARGHCWGPGPTQCVNCSQFLRGQE

CVEECRVLQGLPREYVNARHCLPCHPECQPQNGSVTCFGPEADQCVACA

HYKDPPFCVARCPSGVKPDLSYMPIWKFPDEEGACQPCPINCTHSCVDL

DDKGCPAEQRASPLTSFNNFTVSFWLRVPKVSASHLEIVSAVVGIL...

The tetanus toxin epitopes of p2 and p30 sequences are indicated in bold.

CEF cultures were inoculated with MVA-BN and also transfected with pBN146 plasmid DNA. In turn, samples from these cell cultures were inoculated into CEF cultures in medium containing selection drugs, and EGFP-expressing viral clones were isolated by plaque purification. Virus stocks which grew in the presence of the selection drugs and expressed EGFP were designated MVA-BN-mHER2. Generation of MVA-BN-mHER2 and preparation of the virus stock involved twelve (12) sequential passages, including five (5) plaque purifications.

Next, MVA-BN-mHER2 was passaged in CEF cell cultures in the absence of selection drugs. The absence of selection drugs allowed loss of the region encoding the selection genes, gpt and EGFP and the associated promoter (the selection cassette) from the inserted sequence. Recombination resulting in loss of the selection cassette is mediated by the F1 I4L region and a subsection of that region, the F1 repeat (F1 rpt), which flank the selection cassette in plasmid pBN146. These duplicated sequences were included to mediate recombination that results in loss of the selection cassette, leaving only the mHER2 sequence inserted in the I4L intergenic region.

Plaque-purified virus lacking the selection cassette was prepared. Such preparation involved fifteen (15) passages including five (5) plaque purifications.

The presence of the mHER2 sequence and absence of parental MVA-BN virus in MVA-BN-mHER2 stocks was confirmed by PCR analysis, and nested PCR was used to verify the absence of the selection cassette (the gpt and EGFP genes).

Expression of the mHER2 protein was demonstrated in cells inoculated with MVA-BN-mHER2 in vitro. Cultures of chicken embryo fibroblast (CEF) or HeLa cells were inoculated with MVA-BN-mHER2, or MVA-BN, at the dilutions shown, or with TBS buffer. Cells were harvested from the cultures 24 hours later and cell lysates were prepared. Samples were applied to SDS-PAGE gels (NuPAGE® Novex 4% to 12% Bis-Tris gels, Invitrogen), and electrophoresed in MOPS buffer under reducing conditions (dithiothreitol). Two Reference Standards obtained from Pharmexa A/S were included, namely HER-2 Standard, and HER-2 extracellular domain standard (0.3 ug HER-2 ecd). Gels were electroblotted onto nitrocellulose membranes, which were incubated with rabbit anti-HER-2 antiserum (obtained from Pharmexa A/S). Bound HER-2-antibody was revealed with alkaline phosphatase-labeled anti-rabbit antibody and chromogenic substrate (Western Breeze™, Invitrogen).

The results are shown in FIG. 1. The arrows mark the position of protein detected with anti-HER-2 antiserum in lysates from cell cultures inoculated with MVA-BN-mHER2. Antigen was detected in lysates from both cell types inoculated with MVA-BN-mHER2 (denoted by arrows in FIG. 1) that was a similar size to the HER-2 protein reference standards. No proteins were detected in lysates from cultures inoculated with MVA-BN or with Tris Buffer Saline (TBS) that were similar in size to HER-2 protein reference standards.

These data demonstrate expression, in avian and human cells, of mHER2 following inoculation of the cells with MVA-BN-mHER2. Therefore MVA-BN represents an effective delivery vehicle for the expression of transgenic antigens like mHER2 in human cells.

Example 2

Induction of an Anti-Her-2 Immune Response in Mice Treated with MVA-BN-mHER2

Induction of an anti-HER-2 immune response following treatment with MVA-BN-mHER2 was evaluated in both BALB/c and C57BL/6 mice, two mouse strains with different immunological backgrounds or haplotypes. Induction of an anti-HER-2 immune response following treatment with MVA-BN-mHER2 was also evaluated in BALB/c NeuT mice, a transgenic HER-2 mouse strain. In these studies, various doses of MVA-BN-mHER2 ranging from 2E6 to 5E7 $TCID_{50}$ were evaluated as described further below. Blood samples were collected one day prior to each treatment and at various times during and after treatment as described below.

Humoral responses (production of anti-HER-2 IgG) were analyzed by ELISA assay. Splenocytes were collected after the final treatment and cellular responses were analyzed by ELISpot. Those studies are described in Example 3.

Mouse strains: Female BALB/c and C57BL/6 mice aged 8-10 weeks were obtained from HSD. BALB/c NeuT mice were a generous gift from Guido Forni. These mice express an activated HER-2/Neu oncogene under the control of a chimeric mouse mammary tumor virus (MMTV) promoter. BALB/c NeuT females show no morphological abnormalities of the mammary gland until 3 weeks of age. They then progress through atypical hyperplasia to in situ lobular carcinoma. By 25 weeks of age, all 10 mammary glands display invasive carcinomas (Boggio et al, 1998, J. Exp. Med.). All experiments used five to ten mice per group.

Induction of Anti-HER-2 Antibody Responses in Mice Treated with MVA-BN-mHER2

BALB/c, C57BL/6, and BALB/c NeuT mice were injected subcutaneously with control solution (Tris Buffered Saline (TBS)), or with 2E6, 1E7, or 5E7 $TCID_{50}$ of MVA-BN-mHER2 at day 1, 15 and 29. Five animals were in each of those test treatment groups. Blood samples were collected at day 0, 14, 28, 42 and 56. Sera from each of the five animals in each test group were pooled and analyzed for the presence of anti-HER-2 IgG using an ELISA assay.

The ELISA assay was carried out as follows. ELISA plates were first coated with recombinant human ErbB2/Fc Chimera (R+D System, diluted in coating buffer (200 mM Na2CO3, pH 9.6)) at 2 µg/ml (50 µl/well) for one hour at room temperature. Plates were washed with PBS+0.05% Tween six times using a plate washer (Wellwash AC, Thermo Electronics) and subsequently blocked for 1 hour with PBS+0.05% Tween. Plates were washed six times again. Mouse serum was diluted in PBS+0.05% Tween and added at 50 µl/well. Plates were incubated for one hour at room temperature. Plates were then washed 6 times and sheep anti-mouse IgG-HRP secondary antibody (Southern Biotech J3003-VI4513) was added (50 µl/well at 1:1000 diluted in PBS+0.05% Tween). Plates were incubated for one hour at room temperature. Plates were washed six times and then 100 µl/well of TMB substrate was added to all wells. Plates were incubated for twenty minutes in the dark, then 100 µl of 0.5M H2SO4 was added to all wells. Absorbance at 450 nm in each well was determined using a plate reader (Thermo Electronics).

Figure 2:
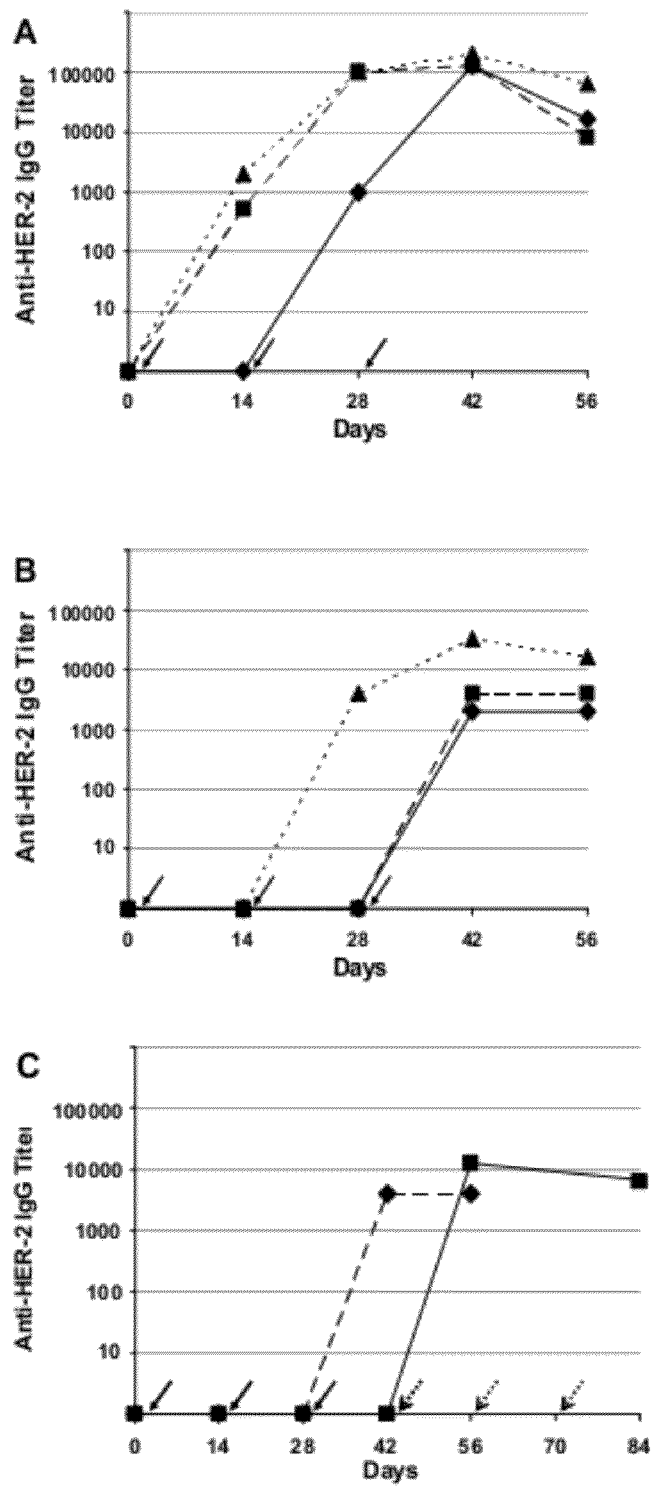
FIG. 2A-C. Anti-HER-2 antibody responses in different mice strains treated with MVA-BN-mHER2. C57BL/6 (A) or BALB/c (B) mice (5 animals in each group) were treated with 2E6 (♦), 1E7 (■) and 5E7 (▲) $TCID_{50}$ MVA-BN-mHER2 at day 1, 15 and 29 (indicated by arrows), as described in Example 2. Blood samples were collected and serial dilutions of pooled sera were analyzed for the presence of anti-HER-2 IgG by ELISA, as described in Example 2. Titers or dilution factors at which signals two fold above background were detected are shown for different time points. (C) BALB/c (♦) and HER-2 transgenic BALB/c NeuT (■) mice were treated with MVA-BN-mHER2 (1E7 $TCID_{50}$). Anti-HER-2 IgG titers were determined as in panels A and B.

The results are shown in FIGS. 2A-C. FIGS. 2A and 2B show that an anti-HER-2 antibody response was detected in all MVA-BN-mHER2-treated groups in both C57BL/6 and BALB/c mice. In both strains, anti-HER-2 antibody titers increased with multiple administrations of MVA-BN-mHER2 and plateaued after treatment ceased. FIG. 2C shows that an anti-HER-2 antibody response was also detected in HER-2 transgenic BALB/c NeuT mice that constitutively express HER-2. Thus, these data demonstrate that MVA-BN-mHER2 is a potent immunogen that can overcome immune tolerance to HER-2, an attribute that can be useful for the treatment of cancer patients.

Antigen Specificity of MVA-BN-mHER2-Induced Anti-Her-2 Antibody Response

Figure 3:
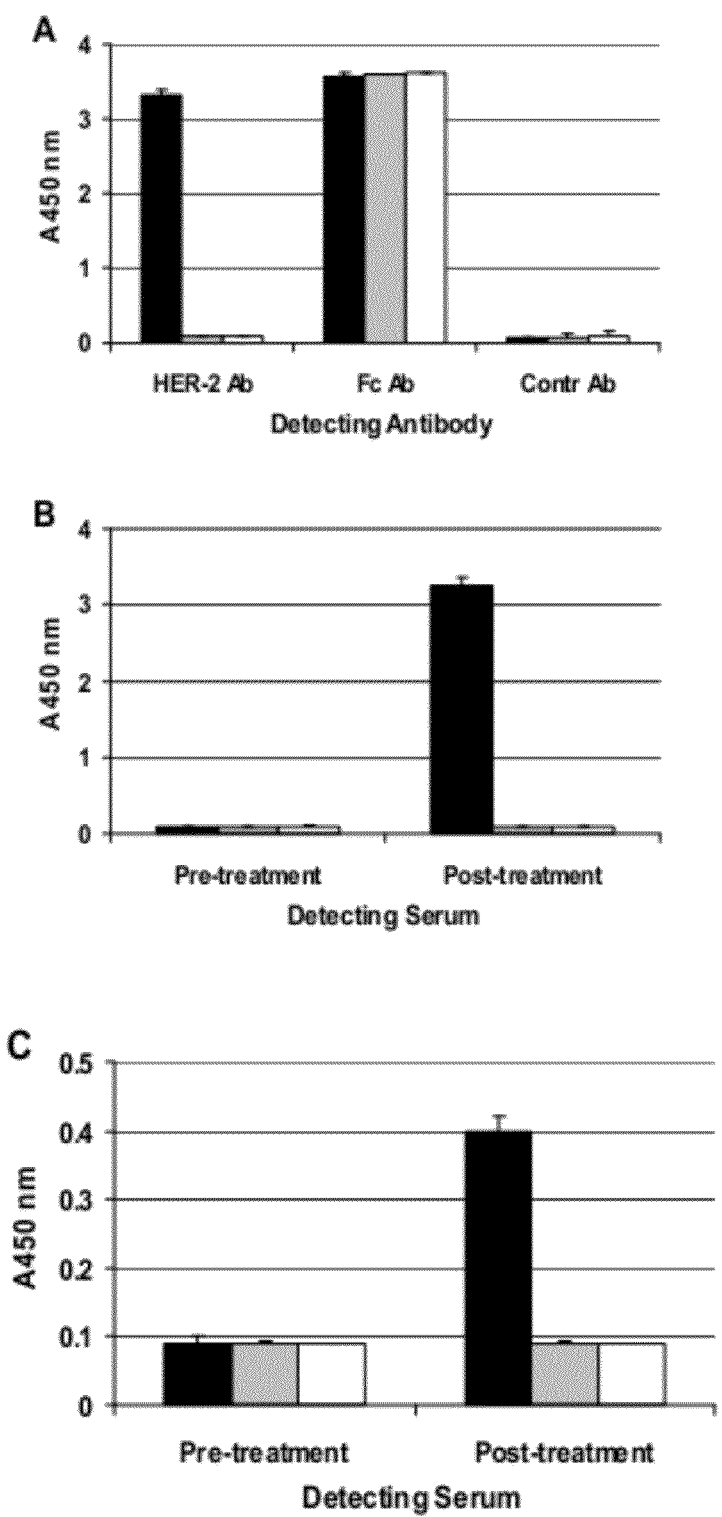
FIG. 3A-C. Antigen specificity of MVA-BN-mHER2-induced anti-HER-2 antibody responses. (A) Wells of a microtitration plate were coated with HER-2 ecd-Fc (black column), HER-3 ecd-Fc (gray column) and HER-4 ecd-Fc (white column), as described in Example 2. Antigens were then detected by ELISA using a monoclonal anti-HER-2 antibody (HER-2 Ab; AB-5, Calbiochem), a monoclonal anti-human Ig Fc fragment antibody (Fc Ab; Southern Biotech) or a monoclonal isotype control antibody (Contr Ab). (B) and (C). ELISA assays were performed using sera from C57BL/6 (B) or BALB/c (C) mice treated with MVA-BN-mHER2 (5E7 $TCID_{50}$). Pre-treatment sera were collected before the first treatment; post-treatment sera were collected at day 42, two weeks after the last of three injections given at two weeks intervals. Data shown are mean±standard deviation, indicated by the standard error bars.

The sera of MVA-BN-mHER2 treated mice were also evaluated by ELISA using the procedure described above. HER-2, HER-3, and HER-4 ecd-Fc chimeric proteins were used as antigens coated onto the wells of a microtitration plate. Antigens were detected using a monoclonal anti-HER-2 antibody (HER-2 Ab; AB-5, Calbiochem), a monoclonal anti-human Ig Fc fragment antibody (Fc Ab; Southern Biotech), or a monoclonal isotype control antibody (Contr Ab). The results are shown in FIG. 3. FIG. 3A shows the ELISA controls: the monoclonal anti-HER-2 antibody specifically reacts with only HER-2 ecd-Fc coated wells, whereas the monoclonal anti-human Ig Fc fragment antibody reacts with all three chimeric proteins. FIGS. 3B and 3C show that in both C57BL/6 and BALB/c mice treated with MVA-BN-mHER2, the sera only detected the HER-2 ecd-Fc chimera. These data show that, in both mouse strains, the antibody response induced after MVA-BN-mHER2 treatment is highly specific to HER-2 and does not cross-react with certain other members of the Epidermal Growth Factor receptor family, such as HER-3 and HER-4.

The induction of anti-HER-2 antibodies in MVA-BN-mHER2 treated mice was also evaluated by fluorescence-activated cell scan (FACS) analysis using a murine cell line expressing human HER-2 (CT26-HER-2; described below). Sera of mice treated with MVA-BN-mHER2 contained antibodies that bound to cells expressing human HER-2, but not to their parental counterparts that do not express this receptor (data not shown).

In summary, these data demonstrate that treatment of mice with MVA-BN-mHER2 stimulates the formation of antibodies which are capable of binding to human HER-2 polypeptides as well as to human HER-2 expressed on the surface of cells.

Example 3

Induction of Anti-Her-2 T-Cell Responses

Figure 4:
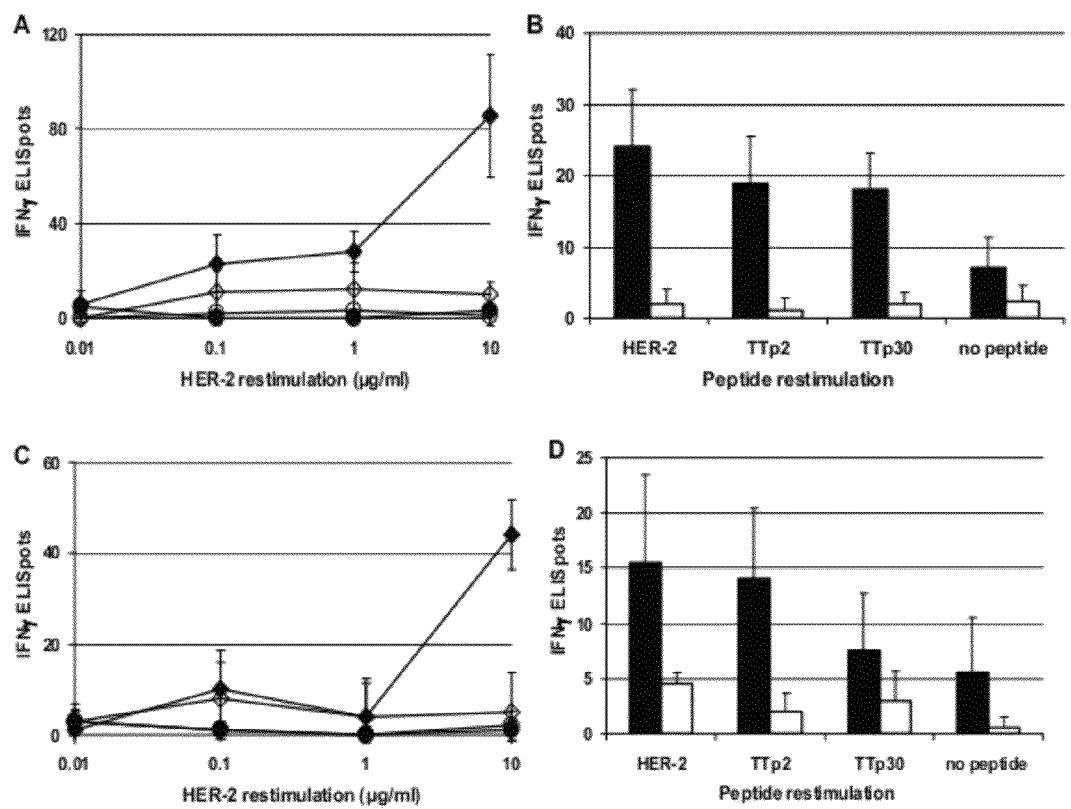
FIG. 4A-D. HER-2-induced T-cell responses in different mice strains treated with MVA-BN-mHER2. C57BL/6 (A and B) or BALB/c (C and D) mice (5 animals in each group) were treated with TBS or 1E7 $TCID_{50}$ MVA-BN-mHER2 as described in Example 3. Five days after the last treatment, spleens were collected and cell suspensions were prepared for in vitro restimulation. Secreted IFNγ was detected by standard ELISpot assay as described in Example 3. A and C, incremental amounts of HER-2 ecd (filled symbols) or medium only (open symbols) were added to spleen cells from mice treated with TBS (circles) or MVA-BN-mHER2 (diamonds). B and D, spleen cells from mice treated with TBS (empty bars) or MVA-BN-mHER2 (black bars) were restimulated with a HER-2 peptide or one of the tetanus toxin peptides (TTp2 or TTp30) as described in Example 3. Data shown are mean±standard deviation, indicated by the standard error bars.

BALB/c and C57BL/6 mice (5 animals in each group) were injected subcutaneously with control (TBS) or 1E7 $TCID_{50}$ of MVA-BN-mHER2 at day 1, 15, 29, and 43. Spleens were harvested from the animals at day 48 and cell suspensions from each test group were pooled for analysis. The induction of T-cell responses was evaluated by an ELISpot assay that measured IFNγ production after in vitro antigen-specific restimulation. HER-2 ecd, a MHC Class I HER-2 peptide, and the two MHC Class II T-helper peptides from tetanus toxin that are included in the mHER2 sequence were used individually for restimulation. The Class I HER-2 peptide had the amino acid sequence, TYLPTNASL (SEQ ID NO:3). The MHC Class II T-helper tetanus toxin peptide P2 had the amino acid sequence, QYIKANSKFIGITEL (SEQ ID NO:4) (labeled TTp2 in FIG. 4) and the MHC Class II T-helper tetanus toxin peptide P30 had the amino acid sequence, FNNFTVSFWLRVPKVSASHLE (SEQ ID NO:5) (labeled TTp30 in FIG. 4).

THE ELISpot assay was performed as follows. Assay plates were prepared by pre-wetting membranes of Millipore Multiscreen 96-well filtration plates by adding 15 µl 35% ethanol to each well. Ethanol was flicked out immediately and the plates were washed twice with 200 µl/well PBS. Plates were coated with rat anti-mouse IFN-γ capture antibody (BD Pharmingen, 551216, lot#34503) at 2 µg/ml (50 µl/well diluted in PBS) and incubated overnight at 4° C. Coating antibody was flicked out and plates were washed three times with PBS under sterile conditions. Plates were blocked with 100 µl/well RPMI-10 (RPMI+10% FCS+β-mercaptoethanol) for at least 30 minutes at room temperature and subsequently washed twice with PBS.

Effector cells were added in 50 µl of RPMI-10 (RPMI+10% FCS+2-ME 5×10−5M+1×Pen/Strep.) at indicated concentrations. HER-2 proteins, HER-2 peptide, or tetanus toxin proteins and peptides were diluted in RPMI-10 and added at appropriate dilutions (usually starting at 10 ug/ml for proteins and 25 µM for peptides, but varied throughout experiments)

to effector wells (50 µl/well). Plates were incubated at 37° C. in a CO₂ incubator for approximately 18 hours.

Cells were flicked out of the wells and 100 µl/well dH₂O was added to all wells for 5 minutes at room temperature. Wells were washed three times with 100 µl/well dH₂O. Plates were then washed with a plate washer (Wellwash AC, Thermo Electron) six times, with PBS+0.05% Tween as washing buffer.

50 µl/well anti-IFN-γ-biotin (Serotec, MCA1548B, batch#0803) at a dilution of 1:5000 in PBS+5% FCS was added to all wells and incubated for one to two hours at room temperature. Plates were then washed using a plate washer (Wellwash AC, Thermo Electron) for 6 cycles, with PBS+ 0.05% Tween as washing buffer. Then 50 µl/well Streptavadin-AlkalinePhosphatase (BD Pharmingen, 554065, lot#46484) at a dilution of 1:5000 in PBS+5% BSA was added to all wells and incubated for one hour at room temperature.

Plates were then washed again using a plate washer (Wellwash AC, Thermo Electron) for 6 cycles and subsequently developed in the dark by adding 50 µl/well BCIP/NBT substrate for 15 minutes. Substrate was flicked out into a sink and washed thoroughly with tap water. Backings of plates were removed and plates were dried in a fume hood. Plates were scanned and read on an ImmunoSpot plate scanner using CellCount Pro software.

The results are shown in FIGS. 4A-D. FIGS. 4A and C show that a dose-dependent T-cell response was detected in spleen cells of both C57BL/6 (FIG. 4A) and BALB/c (FIG. 4C) strains of mice upon restimulation with HER-2 ecd.

FIG. 4B (C57BL/6 mice) and FIG. 4D (BALB/c mice) show that IFNγ production was also detected in this assay following incubation with a HER-2 MHC Class I peptide as well as both tetanus toxin MHC Class II peptides. This result indicates that both MHC Class I-specific CD8 T-cells and MHC Class II-specific CD4 T-cells were induced in mice treated with MVA-BN-mHER2. These data confirm that the tetanus toxin peptides in mHER2 act as T-helper epitopes and indicate that MVA-BN-mHER2 treatment induces T-cells, including CD8 T-cells, that react with epitopes present in the native HER-2 protein.

In summary, these studies show that repeated treatment of mice with MVA-BN-mHER2 induces a broad antigen-specific adaptive immune response that includes antibodies as well as both CD4 and CD8 T-cell subtypes. Similar results were obtained in both C57BL/6 and BALB/c mice indicating that animals with different MHC haplotypes respond similarly. As discussed above in Example 2, a specific antibody response was obtained in HER-2-tolerant mice. Therefore, MVA-BN-mHER2 treatment has the potential to mediate the elimination of self antigen-expressing tumor cells by multiple pathways and in varied MHC environments, which is desirable for cancer treatment. Thus, treatment regimens employing multiple injections of MVA-BN-mHER2 can be used in the treatment of human cancer patients.

Example 4

Th1 Immune Modulation in MVA-BN-mHER2 Treated Mice

The data in the Examples above indicate that MVA-BN is an efficient transgene delivery vehicle that also displays strong immunogenic properties. It has previously been reported that MVA triggers a Th1 adaptive immune responses that confers protection against smallpox (Earl et al., 2004; Wyatt et al., 2004) and also induces innate immune responses (Brutkiewicz et al., 1992; Dokun et al., 2001). Accordingly, the intrinsic immune properties of MVA-BN are potentially useful to modulate immune responses to transgenes.

Examination of certain antibody subtypes produced following administration of immunogens is known to reveal certain characteristics of the immune response. For example, IgG2a antibodies have been shown to be prevalent in Th1 immune environments, whereas IgG1 antibodies are prevalent when a Th2 immune response is induced. Th1 immune environments comprise both humoral and cellular components of the immune response and thus, are conducive to long-lasting protective responses which may be desirable in a cancer immunotherapeutic context. Th2 immune environments, in contrast, comprise short-lived humoral components of the immune response, which are less desirable in a cancer immunotherapeutic context. Thus, measuring the ratio of IgG2a to IgG1 subtypes following administration of an immunogen in mice is a means of assessing the Th1/Th2 characteristics of the immune response. An increase of the IgG2a/IgG1 ratio following administration of an immunogen is an indication of a shift toward a Th1 environment. Conversely, a lower ratio indicates a shift toward a Th2 response.

The ability of MVA-BN-mHER2 to modulate the immune response to HER-2 was assessed by measuring the ratio of anti-HER-2 IgG2a to IgG1 antibody subtypes produced following treatment of mice with various formulations comprising HER-2 sequences. The IgG2a/IgG1 ratio of anti-HER-2 antibodies induced after treatment of BALB/c mice with either MVA-BN-mHER2, mHER2 protein in Freund's adjuvant emulsion, or HER-2 (+) tumor cell lines was determined by ELISA using antibody-subtype-specific detection antibodies. The ELISA assays were performed as described above, except with the substitution of the detection antibodies. The results are shown in Table 1 below.

The results show that the IgG2a/IgG1 ratio was significantly higher in mice treated with MVA-BN-mHER2 compared to mice treated with HER-2 in Freund's adjuvant or HER-2 (+) tumor cells. In addition, the results show that the IgG2a/IgG1 ratio of antibody in serum from mice treated with HER-2 (+) tumor cell lines increased when these mice were co-treated with MVA-BN-mHER2. That result indicates that even in a Th2 environment, which resulted from administration of HER-2 (+) tumor cell lines, the additional administration of MVA-BN-mHER2 effectively induced a Th1 response.

TABLE 1

IgG2a/IgG1 ratio of anti-HER-2 antibody responses induced by various formulations comprising HER-2 sequences.

| Formulation | Mouse treatment | IgG2a/IgG1 ratio* |
| --- | --- | --- |
| MVA-BN-mHER2 | 3 subcutaneous injections at 2 week intervals with doses ranging between 2E6 and 5E7 TCID₅₀ | 0.38 ± 0.09 |
| HER-2 ECD in Freund's Adjuvant | 3 subcutaneous injections at 2 week intervals with 10 µg protein emulsified in CFA then IFA | 0.08 ± 0.02 |
| TUBO cells | 1E5 cells injected intradermally | 0.03 ± 0.02 |
| MC38-HER-2 | 1E5 cells injected intradermally | 0.03 ± 0.02 |
| TUBO cells + MVA-BN-mHER2 | 1E5 cells injected intradermally and 3 subcutaneous injections at 1 week intervals with 5E7 TCID₅₀ MVA-BN-mHER2 (1st dose on same day as cells) | 0.69 ± 0.07 |

TABLE 1-continued

IgG2a/IgG1 ratio of anti-HER-2 antibody responses induced by
various formulations comprising HER-2 sequences.

| Formulation | Mouse treatment | IgG2a/IgG1 ratio* |
|---|---|---|
| MC38-HER-2 + MVA-BN-mHER2 | 1E5 cells injected intradermally and 3 subcutaneous injections at 1 week intervals with 5E7 TCID$_{50}$ MVA-BN-mHER2 (1st dose on same day as cells). | 0.5 ± 0.07 |

*Values represent the mean ± standard deviation of at least two sets of duplicate wells.

In summary, these data demonstrate that the intrinsic immunogenicity of MVA-BN, which is characterized by a strong bias toward Th1 immune responses, influences the immune response against HER-2 toward the Th1 environment. This was true also when there was a Th2-biased anti-HER-2 antibody response induced by tumor cells expressing HER-2. The potent immune modulation property of MVA-BN described here is desirable in a therapeutic context since preexisting anti-HER-2 antibody responses induced by tumors have been reported in breast cancer patients. Thus, even if an undesirable Th2 response towards HER-2 already exists, treatment of patients with MVA-BN-mHER2 should refocus the immune response towards a Th1 profile.

Example 5

Anti-Tumor Activity in Mice Treated with MVA-BN-mHER2

Prophylactic Treatment

The ability of MVA-BN-mHER2 to prevent tumor growth in a prophylactic context was evaluated using transplanted TUBO cells as a breast cancer model in mice. TUBO cells are derived from a mammary gland carcinoma that developed in a BALB/c mouse transgenic for the transforming rat HER-2 (HER-2/neu) oncogene (Rovero et al, *J. Immunol.* 165, 5133-5142 (2000)). Since the HER-2 sequence is highly conserved between rat and human, TUBO cells are used routinely to evaluate efficacy of vaccines comprising either the rat or human homologues of HER-2 (Dela Cruz et al., Vaccine 23, 4793-4803 (2005)).

Figure 5:
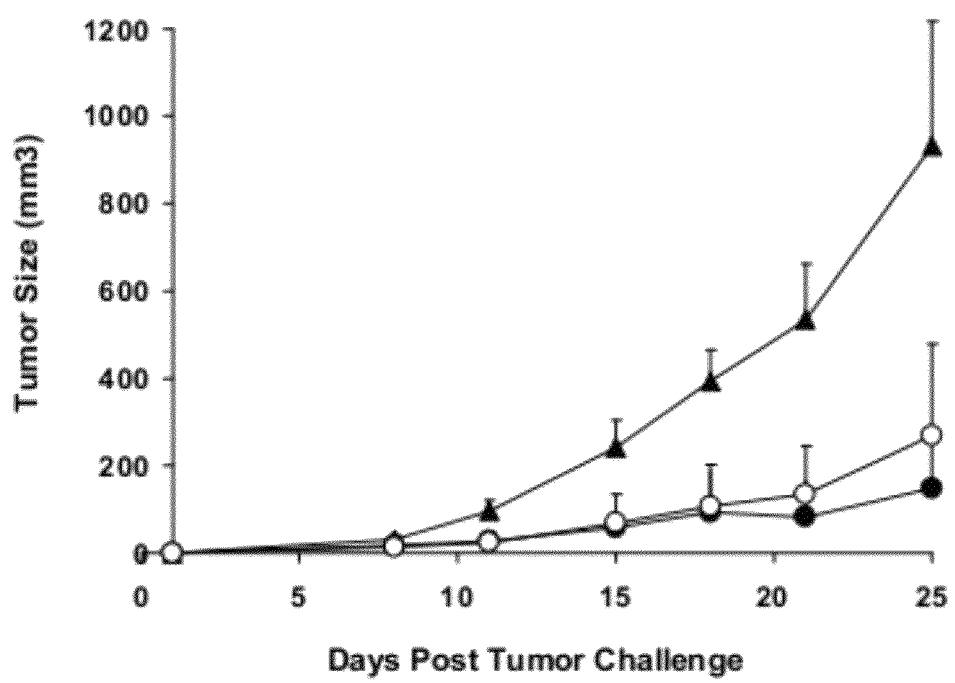
FIG. 5. Analysis of tumor growth in mice pre-treated with MVA-BN-mHER2 (Prophylactic setting). BALB/c mice (5 animals in each group) were injected subcutaneously with TBS (black triangles), MVA-BN-mHER2 (2E7 $TCID_{50}$, black circles) or MVA-BN-mHER2 (2E6 $TCID_{50}$, open circles), as described in Example 5. Six weeks after the last injection, mice were challenged with TUBO (1E5) cells injected intradermally. Tumor growth was determined twice weekly thereafter. Data shown are mean±standard deviation, indicated by the standard error bars.

In this efficacy study, mice where immunized with MVA-BN-mHER2 as described above, i.e., three times at 2-week intervals with either TBS or MVA-BN-mHER2 (2E6 or 5E7 TCID$_{50}$). Treated mice were then subjected to tumor challenge by injecting 3E5 TUBO cells intradermally six weeks after the last vaccine injection. Tumor growth at the injection site was observed twice weekly thereafter and the size of solid tumors under the skin was measured using calipers. Tumor volume (mm3) was calculated using the formula: V=(L×W2)/2, where L=length, W=width, (1 mm3=1 mg). The results presented in FIG. 5 show that the tumors in animals pretreated with MVA-BN-mHER2 were significantly smaller than the tumors in control-treated mice.

The differences in tumor size were statistically-significant in mice that received MVA-BN-mHER2 at either dose, compared to the size of tumors in TBS-treated mice (p<0.005). At day 25, several MVA-BN-mHER2-treated mice showed tumor stabilization, regression or even eradication. Since mice were challenged with tumor cells six weeks following the last MVA-BN-mHER2 treatment, these data show that the observed inhibition of tumor growth was most likely mediated by the recall of a memory immune response induced by MVA-BN-mHER2 administration.

In summary, these data show that treatment of mice with MVA-BN-mHER2 induces an antigen-specific adaptive immune response and the establishment of immune memory. When mice are subsequently challenged subsequently with tumor cells expressing HER-2, the immune memory is recalled and inhibits the growth of the tumor cells.

Therapeutic Treatment: Suppression of Established Tumors by Treatment with MVA-BN-mHER2

The ability of MVA-BN-mHER2 to suppress established tumors was evaluated in an experimental lung metastasis model using CT26 cells stably expressing human HER-2. CT26 is a chemically induced colorectal carcinoma of BALB/c mice (Brattain et al., 1980). In this model, CT26-HER-2 cells are injected intravenously into BALB/c mice and tumor burden is assessed in the lungs where tumor nodules grow.

Mice were challenged with CT26-HER-2 (5E5) cells injected intravenously on day 1 and treated intraperitoneally on day 4 with a single injection of TBS, MVA-BN (5E7 TCID$_{50}$) or MVA-BN-mHER2 (5E7 TCID$_{50}$). Mice were then sacrificed on day 14 and their lungs were weighed. Tumor mass was calculated by subtracting the average lung weight of naïve mice (not challenged with tumor cells) from the average lung weight of tumor-challenged mice.

Figure 6:
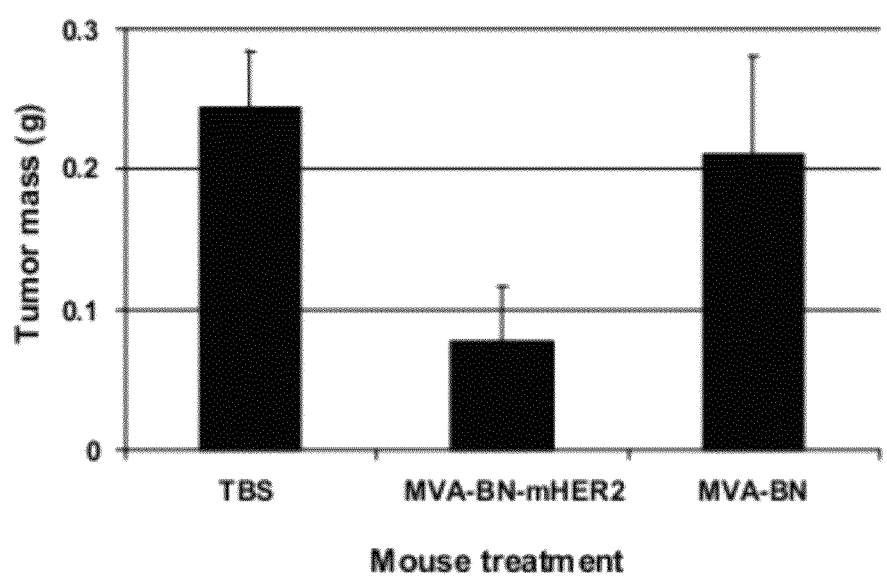
FIG. 6. Analysis of tumor growth in mice treated with MVA-BN-mHER2. BALB/c mice (9 animals in each group) were challenged with CT26-HER-2 (5E5 cells injected intravenously) on day 1 and treated intraperitonally on day 4 with TBS, MVA-BN-mHER2 (5E7 $TCID_{50}$), or MVA-BN (5E7 $TCID_{50}$), as described in Example 5. Mice were sacrificed on day 14 and their lungs weighed. Tumor mass was calculated by subtracting the average lung weight of naïve mice from the average lung weight of tumor challenged mice. Data shown are mean±standard deviation, indicated by the standard error bars.

The results are presented in FIG. 6. The results show that the tumor burden in mice treated with MVA-BN-mHER2 was significantly lower than in control mice (p<0.000001). In fact, sharply decreased lung weight was observed in all animals of the MVA-BN-mHER2 group compared to the control group. In contrast, tumor burden was similar in mice of the control and MVA-BN treated groups. In summary, treatment of mice with MVA-BN-mHER2 inhibits the growth of established HER-2 (+) tumors in mice.

Therapeutic Treatment: Induction of Protective Innate Immunity after Treatment with MVA-BN-mHER2 or MVA-BN The ability of MVA-BN to contribute to the anti-tumor activity of MVA-BN-mHER2 by triggering innate immunity was evaluated in the CT26 tumor model described above. In this experiment, mice were treated with either MVA-BN (5E6 or 5E7 TCID$_{50}$) or MVA-BN-mHER2 (5E6 or 5E7 TCID$_{50}$) on the day of tumor challenge, a time at which the tumor burden is low. Tumor burden was assessed as described above in the lungs of challenged mice. The results are presented in FIG. 7. The results show that tumor growth inhibition (TGI) by treatment with MVA-BN (5E7 TCID$_{50}$) was >70% (p<0.0001). The anti-tumor activity of MVA-BN was dose-dependent since treatment with of MVA-BN (5E6 TCID$_{50}$) was less efficient (32% TGI; p=0.002) than treatment with 5E7 TCID$_{50}$. In contrast, mice treated with MVA-BN-mHER2 (either 5E6 or 5E7 TCID$_{50}$) displayed similar protection (>70% TGI; p<0.000001).

Figure 7:
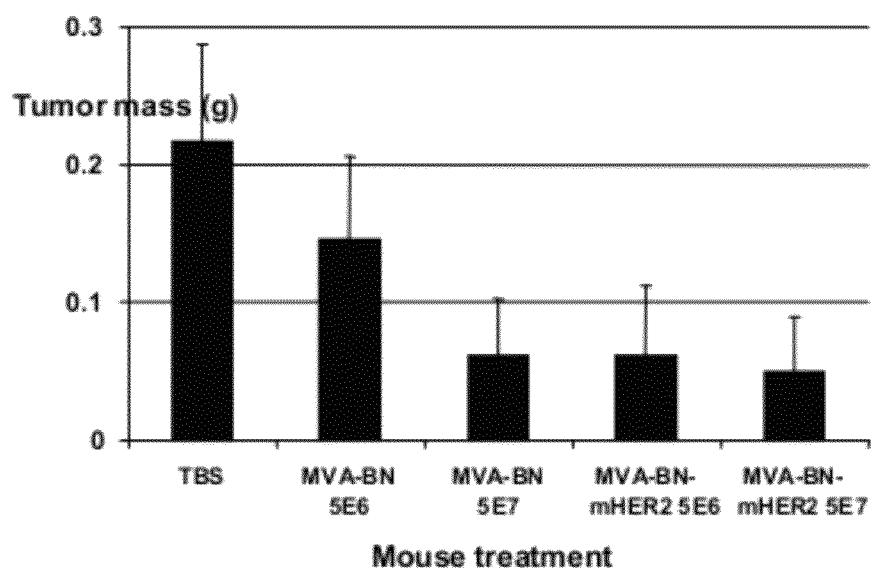
FIG. 7. Analysis of tumor growth in mice treated with MVA-BN-mHER2 or MVA-BN. BALB/c mice (9 animals in each group) were challenged with CT26-HER-2 (5E5 cells injected intravenously) on day 1 and treated intraperitonally the same day with TBS, MVA-BN (5E6 or 5E7 $TCID_{50}$) or MVA-BN-mHER2 (5E6 or 5E7 $TCID_{50}$), as described in Example 5. Mice were sacrificed on day 14 and their lungs weighed. Tumor mass was calculated by subtracting the average lung weight of naive mice from the average lung weight of tumor challenged mice. Data shown are mean±standard deviation, indicated by the standard error bars.

Taken together, the data shown in FIGS. 6 and 7 demonstrate that both MVA-BN and MVA-BN-mHER2 have anti-tumor activity, yet the activity of MVA-BN-mHER2 is superior. Indeed, treatment of mice in the pulmonary metastases model on day 1 (FIG. 7) with MVA-BN-mHER2 (5E6 TCID$_{50}$) was more effective than treatment with the same dose of MVA-BN. In this model, treatment of mice on day 4 (FIG. 6) with MVA-BN-mHER2 also suppressed tumor growth whereas MVA-BN had no effect. Thus, the anti-tumor activity of MVA-BN observed in certain settings is most likely due to the stimulation of innate immunity. The superior activity of MVA-BN-mHER2 observed in all the experiments is likely due to the combined stimulation of the innate immune system and induction of a specific anti-HER-2 adaptive immune response.

Example 6

Combination Therapy with Cytotoxic Agents

C57BL/6 mice were treated subcutaneously with control (Tris Buffered Saline (TBS); I group of 5 animals) or with 5E7 $TCID_{50}$ of MVA-BN-mHER2 (9 groups of 5 animals) at day 1, 22 and 43 (q3 weeks×3). The effect of the chemotherapeutic agent docetaxel on anti-HER-2 antibody induction was evaluated by treating animals with the drug at tumoricidal doses (33 mg/Kg) one week (day −7) or two days (day −2) prior to MVA-BN-mHER2 treatment. The drug was injected iv either once, twice (q3 weeks×2), three (q3 weeks×3) or four times (q3 weeks×4). The animal group arrangement, administration regimen and schedule are summarized in Table 2.

TABLE 2

Study Groups

| Treatment Groups (n = 5) | docetaxel Regimen (33 mg/Kg) | | | Vaccine Regimen |
|---|---|---|---|---|
| | Type | Schedule | Route | |
| 1 | None | N/A | N/A | None |
| 2 | None | N/A | N/A | MVA-BN-mHER2 (5E7 $TCID_{50}$, SC @ d1, 22 & 43) |
| 3 | Doc d-2 X1 | d-2 | IV | MVA-BN-mHER2 (5E7 $TCID_{50}$, SC @ d1, 22 & 43) |
| 4 | Doc d-2 X2 | d-2 & d20 | IV | MVA-BN-mHER2 (5E7 $TCID_{50}$, SC @ d1, 22 & 43) |
| 5 | Doc d-2 X3 | d-2, d20 & d41 | IV | MVA-BN-mHER2 (5E7 $TCID_{50}$, SC @ d1, 22 & 43) |
| 6 | Doc d-2 X4 | d-2, d20, d41 & d62 | IV | MVA-BN-mHER2 (5E7 $TCID_{50}$, SC @ d1, 22 & 43) |
| 7 | Doc d-8 X1 | d-7 | IV | MVA-BN-mHER2 (5E7 $TCID_{50}$, SC @ d1, 22 & 43) |
| 8 | Doc d-8 X2 | d-7 & d15 | IV | MVA-BN-mHER2 (5E7 $TCID_{50}$, SC @ d1, 22 & 43) |
| 9 | Doc d-7 X3 | d-7, d15 & d36 | IV | MVA-BN-mHER2 (5E7 $TCID_{50}$, SC @ d1, 22 & 43) |
| 10 | Doc d-7 X4 | d-7, d15, d36 & d57 | IV | MVA-BN-mHER2 (5E7 $TCID_{50}$, SC @ d1, 22 & 43) |

Figure 8:
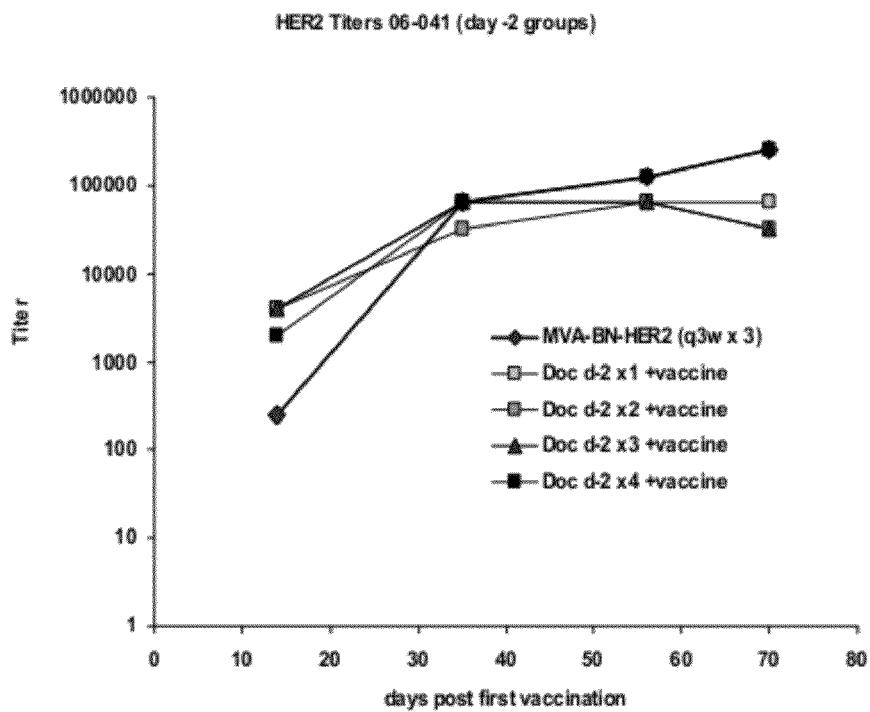
FIG. 8 A-B. Anti-HER-2 antibody responses in mice co-treated with MVA-BN-mHER2 and docetaxel. C57BL/6 mice were treated subcutaneously with control (Tris Buffered Saline (TBS); 1 group of 5 animals) or with 5E7 $TCID_{50}$ of MVA-BN-mHER2 (9 groups of 5 animals) at day 1, 22 and 43 (q3 weeks×3). The effect of the chemotherapeutic agent docetaxel on anti-HER-2 antibody induction was evaluated by treating animals with the drug at tumoricidal doses (33 mg/Kg) two days (day –2) (A) or one week (day –7) (B) prior to MVA-BN-mHER2 treatment. The drug was injected iv either once, twice (q3 weeks×2), three (q3 weeks×3) or four times (q3 weeks×4) as described in Table 2.
Figure 8:
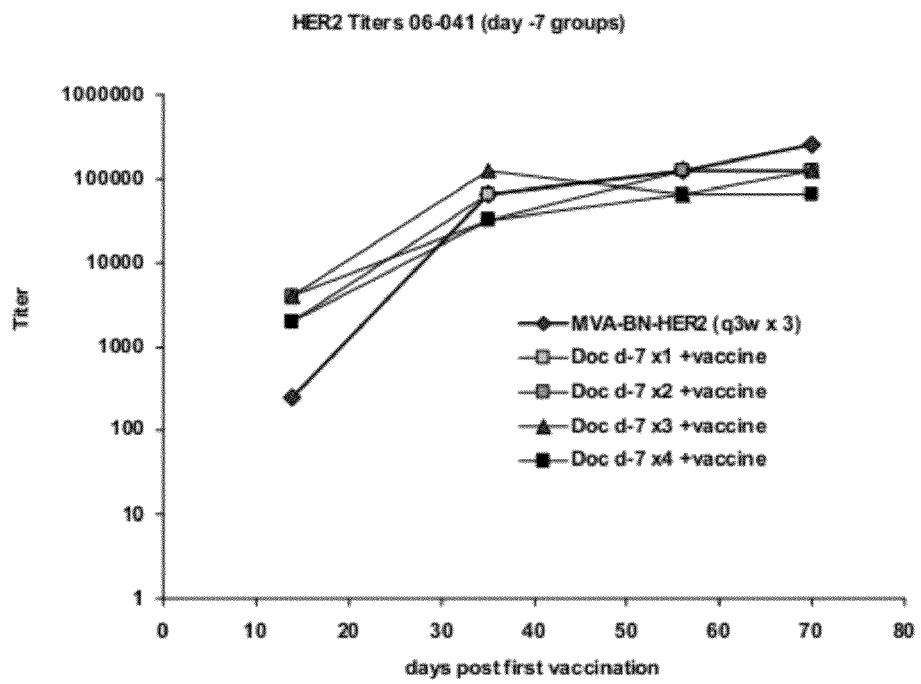

Blood samples were collected at day −9 (pre-bleed), 13 days post each vaccine treatment (d14, 35, 56) and one week after the last drug treatment (d70). Sera from each test group were pooled and analyzed by ELISA using a commercially available HER-2 ecd-Fc chimeric protein as antigen coated onto the wells of a microtitration plate. This chimeric protein comprises the extracellular domain of native human HER-2 fused to the Fc domain of a human immunoglobulin G. As shown in FIGS. 8A and B, an anti-HER-2 antibody response was detected in all MVA-BN-mHER2-treated groups and for each time point, the titers were not significantly different when mice were pretreated two or seven days before vaccination with tumoricidal doses of docetaxel (33 mg/Kg). Moreover the antibody responses were not affected even when the docetaxel treatment continued throughout the three-vaccination schedule.

Figure 9:
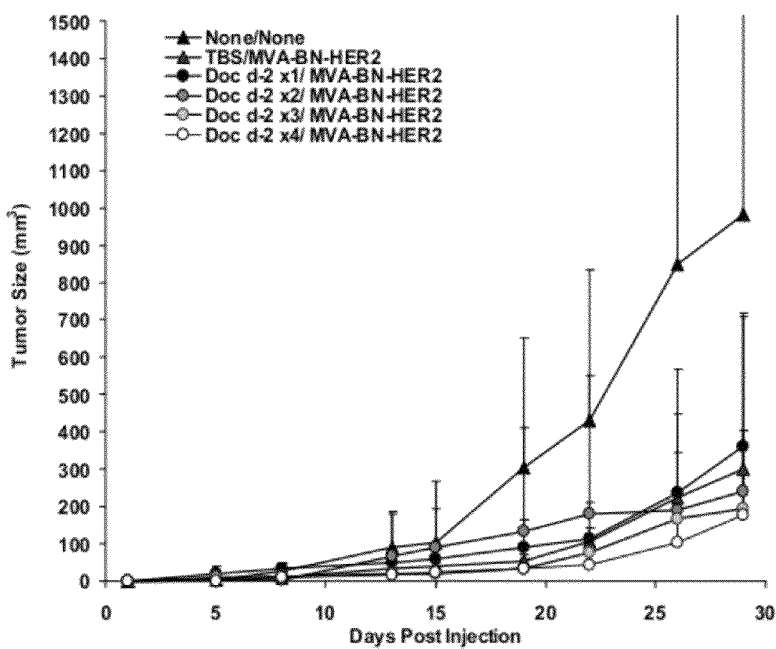
FIG. 9 A-B. Analysis of tumor growth in mice pre-treated with docetaxel and MVA-BN-mHER2 (Prophylactic setting). The integrity of the immune response induced by MVA-BN-mHER2 in mice treated with tumoricidal doses of docetaxel was further evaluated by measuring the anti-tumor activity of MVA-BN-mHER2. Mice treated as described in legend of FIG. 8 were challenged with MC38-HER-2 tumor cells at day 71 and tumor growth was evaluated as described in legend of FIG. 5.
Figure 9:
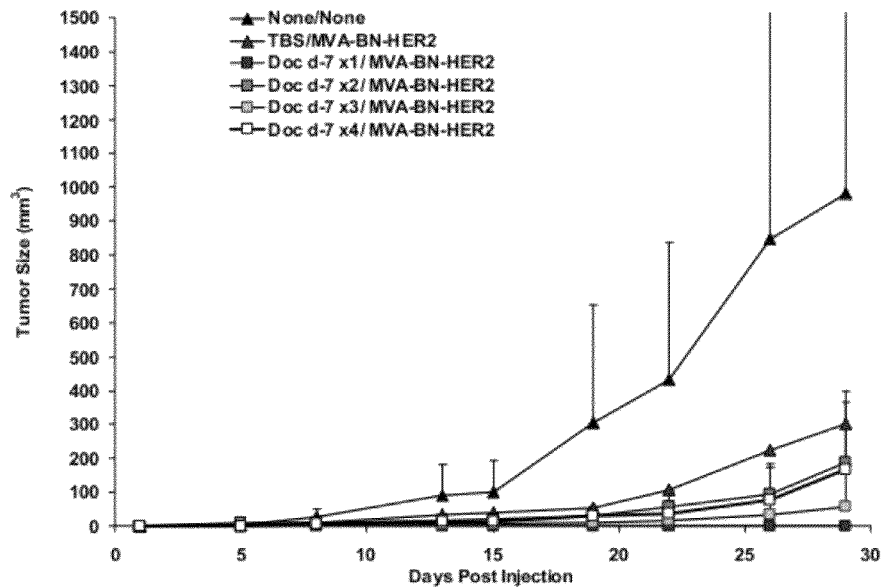

The integrity of the immune response induced by MVA-BN-mHER2 in mice treated with tumoricidal doses of docetaxel was further evaluated by measuring the anti-tumor activity of MVA-BN-mHER2. Indeed, MVA-BN-mHER2 was shown earlier (Example 5) to induce memory responses capable of delaying growth of tumors implanted post vaccination (prophylactic tumor model). Mice of the study groups in Table 2 above were therefore challenged with MC38-HER-2 tumor cells (Penichet et al., Laboratory Animal Science 49, 179-188 (1999)) at day 71 and tumor growth was evaluated as described in Example 5. As shown FIGS. 9A and B, tumor growth was delayed in all mice groups treated with MVA-BN-mHER2. Pretreatment as well as concomitant treatment with docetaxel at tumoricidal doses had no significant effect on tumor growth delay. Because this experiment was performed in a prophylactic setting, the anti-tumor effect measured was most likely mediated by MVA-BN-mHER2-induced anti-HER-2 immune responses while docetaxel had no direct cytotoxic effect on the tumor. Indeed, the shortest time interval between docetaxel treatment and tumor challenge was nine days (Group 6 received its final docetaxel dose on day 62). Given the pharmacological properties of chemotherapeutic agents, the drug concentration was likely too low at time of tumor implantation to be efficacious. Hence, the data confirmed that MVA-BN-mHER2 and docetaxel combined treatment is not detrimental to the induction of protective immune response by the vaccine. This is true even when the chemotherapeutic agent was used at tumoricidal doses at three weeks intervals, which mirrors standard treatment regimen in humans.

The potential benefit provided by combination treatment of chemotherapy and immunotherapy was then evaluated in a therapeutic setting of the mouse MC38-HER-2 tumor model. In this experiment, animals were divided in three subsets (Subset A, B and C) where one chemotherapy treatment was given either before, during or following two immunotherapy treatments, respectively.

Figure 10:
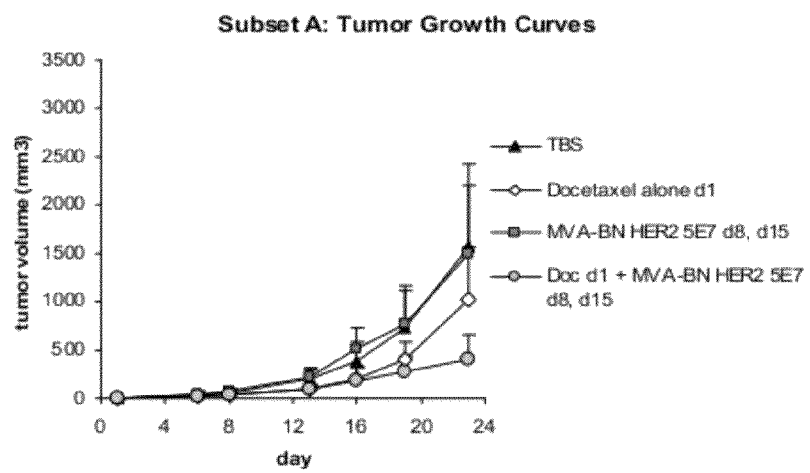
FIG. 10A-C. Analysis of tumor growth in mice co-treated with docetaxel and MVA-BN-mHER2. For each experimental subset A, B and C, C57BL/6 mice (40 animals) were challenged with MC38-HER-2 cells at day 1 then treated subcutaneously with either control (Tris Buffered Saline (TBS); 10 animals treated 3 times), docetaxel alone (33 mg/Kg; 10 animals treated once), MVA-BN-mHER2 (5E7 TCID50; 10 animals treated twice) or docetaxel (1 treatment) and MVA-BN-mHER2 (two treatments) at varied times for each experimental subset as indicated in the Figure. Tumor growth was evaluated twice a week until sacrifice at day 23.
Figure 10:
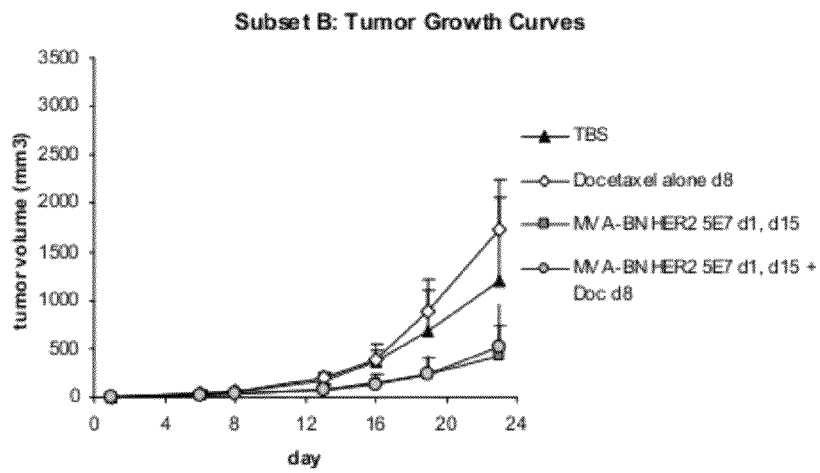
Figure 10:
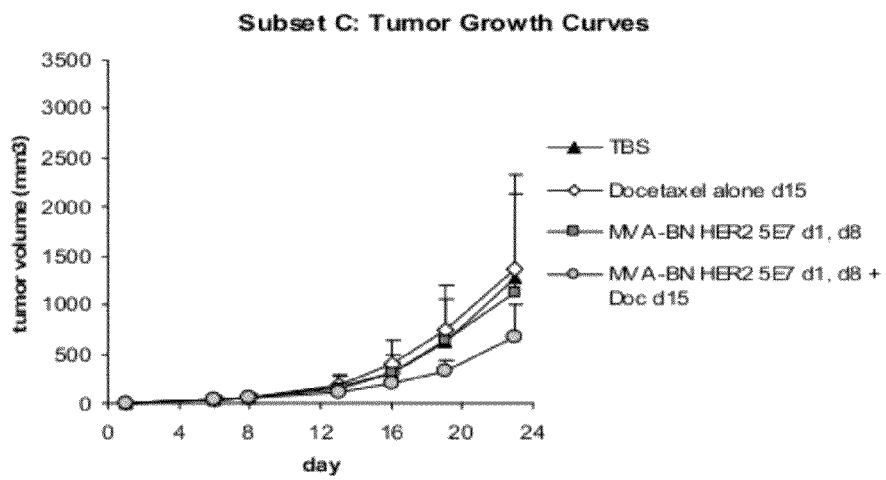

In subset A, C57BL/6 mice (40 animals) were challenged with MC38-HER-2 cells at day 1 then treated subcutaneously with either control (Tris Buffered Saline (TBS); 10 animals treated on d1, 8 and 15), Docetaxel alone (33 mg/Kg; 10 animals treated on d1), MVA-BN-mHER2 (5E7 TCID50; 10 animals treated on d8 and 15) or Docetaxel on day 1 then MVA-BN-mHER2 on d8 and 15. Tumor growth was evaluated twice a week until sacrifice at day 23. As shown in FIG. 10A, Docetaxel treatment on day 1 resulted in a modest and transient delay of tumor growth (statistically significant difference was detected until day 19 only) whereas MVA-BN-mHER2 treatment on day 8 and 15 had no effect on tumor growth. In contrast, the combined treatment of Docetaxel (d1) prior to MVA-BN-mHER2 administration at d8 and 15 was highly efficient at inhibiting tumor growth throughout the study (p=0.001 at day 23).

For subset B, the experiment was performed with the same 4 animal groups; however Docetaxel was given on d8 whereas MVA-BN-mHER2 was administered on day 1 and 15. It was previously determined that Docetaxel had no effect on MC38-HER-2 growth once tumor size exceeds 50 mg in weight, which is reached around day 8 for this model. As expected, Docetaxel treatment at day 8 had no effect on tumor growth (FIG. 10B) whereas two administration of MVA-BN-mHER2 at two weeks interval (on day 1 and day 15) was highly efficient at inhibiting tumor growth (p=0.002 at day 23). More importantly, this anti-tumor activity was not negatively affected by high doses of Docetaxel administrated between the vaccine treatments (FIG. 10B).

For subset C, the experiment was also performed with the same 4 animal groups; however Docetaxel was given on d15 whereas MVA-BN-mHER2 was administered on day 1 and 8. Like for Subset B, the tumors in all groups exceeded the size limit beyond which Docetaxel is non-efficacious at reducing MC38-HER-2 growth at the time of chemotherapy treatment (day 15). And as expected, FIG. 10C, shows that docetaxel had no effect on tumor growth when administered alone. Like in Subset A, vaccine treatment consisting of two administrations of MVA-BN-mHER2 at one week interval was also suboptimal and had no effect on tumor growth as well. Surprisingly, the mean tumor size of the mice from MVA-BN-mHER2-treated group that also received Docetaxel following the vaccine administration was significantly smaller (p=0.036 at day 23) than the mean of tumor size of mice treated with MVA-BN-mHER2 only. This data shows that MVA-BN-mHER2 treatment increases the sensitivity of MC38-HER2 to Docetaxel in vivo.

Overall the data show that MVA-BN-mHER2 and tumoricidal doses of chemotherapeutic agents can be combined with no detrimental effects on the potency of the vaccine. In fact, it was found that combining these two therapies may be mutually beneficial since chemotherapy pre-treatment increased vaccine efficacy whereas vaccine pre-treatment increased the sensitivity of tumor cells to chemotherapy. It is therefore anticipated that combined treatment of continued alternated administration of vaccine and chemotherapy also provide a new means to generate more potent regimen for the treatment of cancer.

Example 7

Epitope/Antigen Spreading

Epitope/antigen spreading results from the induction of immune responses triggered by exposure of epitopes/antigens from dying tumor cells. Vaccine-induced epitope/antigen spreading is highly advantageous for maximal anti-tumor activity. It was found that MVA-BN-mHER2 treatment results in epitope/antigen spreading since mice protected against HER-2+ tumor resist a second challenge with the parental tumor that do not express HER-2. Hence, MVA-BN-mHER2 enables the triggering of a broad protective immune response that can spread to tumor antigens other than HER-2, which is a prerequisite to treat heterogeneous tumors and prevent tumor escape.

Example 8

Spontaneous Tumors in NeuT Mice

A high titer and broad spectrum of antibody is required to delay spontaneous tumors arising in transgenic mice expressing rat HER-2/neu (NeuT mice) treated with heterologous HER-2 (eg. Human HER-2). Vaccine formulation of heterologous HER-2 like naked DNA failed to delay tumor growth in this models whereas viral-based formulation displayed antitumor activity. It was found that MVA-BN-mHER2 delayed spontaneous tumor growth in NeuT even when treatment was started during the later stages of tumor development. Hence, MVA-BN provides a superior antigen formulation for the induction of anti-tumor activity.

We claim:

1. A method for stimulating the formation of antibodies which are capable of binding to human HER-2 expressed on the surface of cells comprising providing a recombinant MVA encoding a polypeptide comprising a human HER-2 antigen for administration to a human cancer patient; wherein the administration stimulates the formation of antibodies which are capable of binding to human HER-2 expressed on the surface of cells; and wherein the antibodies produce a measurable reduction in tumor size or tumor mass compared to patients not administered the recombinant MVA encoding a polypeptide comprising a human HER-2 antigen.

2. The method of claim 1, wherein the MVA is MVA-BN.

3. The method of claim 1, wherein the HER-2 antigen comprises SEQ ID NO:2.

4. The method of claim 2, wherein the HER-2 antigen comprises SEQ ID NO:2.

5. The method of claim 1, further comprising administering a tumoricidal dose of docetaxel to the human cancer patient.

6. The method of claim 2, further comprising administering a tumoricidal dose of docetaxel to the human cancer patient.

7. The method of claim 3, further comprising administering a tumoricidal dose of docetaxel to the human cancer patient.

8. The method of claim 4, further comprising administering a tumoricidal dose of docetaxel to the human cancer patient.

9. The method of claim 1, wherein the human cancer patient is a breast cancer patient.

10. The method of claim 2, wherein the human cancer patient is a breast cancer patient.

11. The method of claim 3, wherein the human cancer patient is a breast cancer patient.

12. The method of claim 4, wherein the human cancer patient is a breast cancer patient.

13. The method of claim 5, wherein the human cancer patient is a breast cancer patient.

14. The method of claim 1, wherein the administration induces T-cells that react with epitopes present in the native HER-2 protein.

15. A method for inducing T-cells that react with epitopes present in the native HER-2 protein comprising providing a recombinant MVA encoding a polypeptide comprising a HER-2 antigen for administration to a human cancer patient; wherein the administration induces T-cells that react with epitopes present in the native HER-2 protein; and wherein the T-cells produce a measurable reduction in tumor size or tumor mass compared to patients not administered the recombinant MVA encoding a polypeptide comprising a human HER-2 antigen.

16. The method of claim 15, wherein the MVA is MVA-BN.

17. The method of claim 15, wherein the HER-2 antigen comprises SEQ ID NO:2.

18. The method of claim 16, wherein the HER-2 antigen comprises SEQ ID NO:2.

19. The method of claim 15, further comprising administering a tumoricidal dose of docetaxel to the human cancer patient.

20. The method of claim 16, further comprising administering a tumoricidal dose of docetaxel to the human cancer patient.

21. The method of claim 17, further comprising administering a tumoricidal dose of docetaxel to the human cancer patient.

22. The method of claim 18, further comprising administering a tumoricidal dose of docetaxel to the human cancer patient.

23. The method of claim 15, wherein the human cancer patient is a breast cancer patient.

24. The method of claim 16, wherein the human cancer patient is a breast cancer patient.

25. The method of claim 17, wherein the human cancer patient is a breast cancer patient.

26. The method of claim 18, wherein the human cancer patient is a breast cancer patient.

27. The method of claim 19, wherein the human cancer patient is a breast cancer patient.

28. The method of claim 15, wherein the administration induces antibodies which are capable of binding to human HER-2 expressed on the surface of cells.

29. A method for stimulating the formation of antibodies which are capable of binding to human HER-2 expressed on the surface of cells comprising providing a recombinant MVA encoding a polypeptide comprising a human HER-2 antigen for administration to a human cancer patient; wherein the administration stimulates the formation of antibodies which are capable of binding to human HER-2 expressed on the surface of cells; and wherein the ratio of immunoglobulin isotype G2a (IgG2a) antibodies to immunoglobulin isotype G1 (IgG1) antibodies is measurably higher in patients administered the recombinant MVA encoding a polypeptide comprising a human HER-2 antigen compared to patients not administered the recombinant MVA encoding a polypeptide comprising a human HER-2 antigen.

30. The method of claim 29, wherein the MVA is MVA-BN.

31. The method of claim 29, wherein the HER-2 antigen comprises SEQ ID NO:2.

32. The method of claim 30, wherein the HER-2 antigen comprises SEQ ID NO:2.

33. The method of claim 29, further comprising administering a tumoricidal dose of docetaxel to the human cancer patient.

34. The method of claim 30, further comprising administering a tumoricidal dose of docetaxel to the human cancer patient.

35. The method of claim 31, further comprising administering a tumoricidal dose of docetaxel to the human cancer patient.

36. The method of claim 32, further comprising administering a tumoricidal dose of docetaxel to the human cancer patient.

37. The method of claim 29, wherein the human cancer patient is a breast cancer patient.

38. The method of claim 30, wherein the human cancer patient is a breast cancer patient.

39. The method of claim 31, wherein the human cancer patient is a breast cancer patient.

40. The method of claim 32, wherein the human cancer patient is a breast cancer patient.

41. The method of claim 33, wherein the human cancer patient is a breast cancer patient.

42. The method of claim 29, wherein the administration induces T-cells that react with epitopes present in the native HER-2 protein.

43. A method for inducing T-cells that react with epitopes present in the native HER-2 protein comprising providing a recombinant MVA encoding a polypeptide comprising a HER-2 antigen for administration to a human cancer patient; wherein the administration induces T-cells that react with epitopes present in the native HER-2 protein; wherein the T-cells are predominantly $T_H1$ T-cells as determined by comparing the ratio of IgG2a to IgG1 antibodies in patients administered the recombinant MVA encoding a polypeptide expressing a HER-2 antigen to the ratio of IgG2a to IgG1 antibodies in patients not administered the recombinant MVA encoding a polypeptide comprising a human HER-2 antigen; and wherein a measurably higher ratio of IgG2a to IgG1 antibodies after administration of the HER-2 antigen indicates a predominantly $T_H1$ T-cell response.

44. The method of claim 43, wherein the MVA is MVA-BN.

45. The method of claim 43, wherein the HER-2 antigen comprises SEQ ID NO:2.

46. The method of claim 44, wherein the HER-2 antigen comprises SEQ ID NO:2.

47. The method of claim 43, further comprising administering a tumoricidal dose of docetaxel to the human cancer patient.

48. The method of claim 44, further comprising administering a tumoricidal dose of docetaxel to the human cancer patient.

49. The method of claim 45, further comprising administering a tumoricidal dose of docetaxel to the human cancer patient.

50. The method of claim 46, further comprising administering a tumoricidal dose of docetaxel to the human cancer patient.

51. The method of claim 43, wherein the human cancer patient is a breast cancer patient.

52. The method of claim 44, wherein the human cancer patient is a breast cancer patient.

53. The method of claim 45, wherein the human cancer patient is a breast cancer patient.

54. The method of claim 46, wherein the human cancer patient is a breast cancer patient.

55. The method of claim 47, wherein the human cancer patient is a breast cancer patient.

56. The method of claim 43, wherein the administration induces antibodies which are capable of binding to human HER-2 expressed on the surface of cells.

* * * * *

```
                             SEQUENCE LISTING

<160> NUMBER OF SEQ ID NOS: 2

<210> SEQ ID NO 1
<211> LENGTH: 2528
<212> TYPE: DNA
<213> ORGANISM: Artificial Sequence
<220> FEATURE:
<223> OTHER INFORMATION: HER2 mRNA expresion vector

<400> SEQUENCE: 1
agtatgcatt tttacggatg gagtctcggt ctaaaaacgg gaatgtacta tctacgtacg      60 aaaccogcat ccgctcccat tcaattcaca ttggacaagg ataaaataaa accactggtg     120
gtttgcgatt ccgaaatctg tacatcatgc agtggttaaa caaatctaga actagtttaa     180
ttaaggagct gttttgaata aaatttttt ataataaatc tagaactagt ggatccccg      240 ggctgcagga attcgatcta gccgccacca tggagctggc ggccttgtgc cgctgggggc     300
tcctcctcgc cctcttgccc cccggagccg cgagcaccca agtgtgcacc ggcacagaca     360
tgaagctgcg gctccctgcc agtcccgaga cccacctgga catgctccgc cacctctacc     420
agggctgcca ggtggtgcag ggaaacctgg aactcaccta cctgcccacc aatgccagct     480
taagtttcct gcaggatatc caggaggtgc agggctacgt gctcatcgct cacaaccaag     540
tgaggcaggt cccactgcag aggctgcgga ttgtgcgagg cacccagctc tttgaggaca     600
actatgccct ggccgtgcta gacaatggag acccgctgaa caataccacc cctgtcacag     660
gggcctcccc aggaggcctg cgggagctgc agcttcgaag cctcacagag atcttgaaag     720
gaggggtctt gatccagcgg aacccccagc tctgctacca ggacacgatt ttgtggaagg     780
acatcttcca caagaacaac cagctggctc tcacactgat agacaccaac cgctctcggg     840
cctgccaccc ctgttctccg atgtgtaagg gctcccgctg ctgggagag agttctgagg     900
```

```
attgtcagag cctgacgcgc actgtctgtg ccggtggctg tgcccgctgc aaggggccac    960
tgcccactga ctgctgccat gagcagtgtg ctgccggctg cacgggcccc aagcactctg   1020
actgcctggc ctgcctccac ttcaaccaca gtggcatctg tgagctgcac tgcccagccc   1080
tggtccagta catcaaagct aactccaaat tcatcggtat caccgagctg cggtatacat   1140
tcggcgccag ctgtgtgact gcctgtccct acaactacct ttctacggac gtgggatcct   1200
gcacccctcgt ctgccccctg cacaaccaag aggtgacagc agaggatgga acacagcggt   1260
gtgagaagtg cagcaagccc tgtgcccgag tgtgctatgg tctgggcatg gagcacttgc   1320
gagaggtgag ggcagttacc agtgccaata tccaggagtt tgctggctgc aagaagatct   1380
tgggagcct ggcatttctg ccggagagct tgatgggga cccagcctcc aacactgccc   1440
cgctccagcc agagcagctc caagtgtttg agactctgga agagatcaca ggttacctat   1500
acatctcagc atggccggac agcctgcctg acctcagcgt cttccagaac ctgcaagtaa   1560
tccggggacg aattctgcac aatggcgcct actcgctgac cctgcaaggg ctgggcatca   1620
gctggctggg gctgcgctca ctgagggaac tgggcagtgg actggccctc atccaccata   1680
acacccacct ctgcttcgtg cacacggtgc cctgggacca gctctttcgg aacccgcacc   1740
aagctctgct ccacactgcc aaccggccag aggacgagtg tgtgggcgag ggcctggcct   1800
gccaccagct gtgcgcccga gggcactgct ggggtccagg gccacccag tgtgtcaact   1860
gcagccagtt ccttcggggc caggagtgcg tggaggaatg ccgagtactg caggggctcc   1920
ccagggagta tgtgaatgcc aggcactgtt tgccgtgcca ccctgagtgt cagccccaga   1980
atggctcagt gacctgtttt ggaccggagg ctgaccagtg tgtggcctgt gcccactata   2040
aggaccctcc cttctgcgtg gcccgctgcc ccagcggtgt gaaacctgac ctctcctaca   2100
tgcccatctg gaagtttcca gatgaggagg gcgcatgcca gccttgcccc atcaactgca   2160
cccactcctg tgtggacctg gatgacaagg gctgccccgc cgagcagaga gccagccctc   2220
tgacgtcctt caacaacttc accgtgagct ctctggctgcg cgtgcccaag gtgagcgcca   2280
gccacctgga gatcgtctct gcggtggttg gcattctgta aagcttggt accgagctcg   2340
gatccactag tccagtgtgg tggaattctg cagatatcca gcacagtggc ggccatcaag   2400
cttatcgata ccgtcgacct cgagggggggg cccggtaccc agttaattaa ggatcccccg   2460
ggctgcagga attccatttt tattctcaaa tgagataaag tgaaaatata tatcatatat   2520
acaaagta                                                            2528
```

<210> SEQ ID NO 2
<211> LENGTH: 683
<212> TYPE: PRT
<213> ORGANISM: Artificial Sequence
<220> FEATURE:
<223> OTHER INFORMATION: mHER2 polypeptide

<400> SEQUENCE: 2

Met Glu Leu Ala Ala Leu Cys Arg Trp Gly Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

```
Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
            115                 120                 125

Val Thr Gly Ala Ser Pro Gly Gly Leu Arg Glu Leu Gln Leu Arg Ser
130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
            195                 200                 205

Ser Glu Asp Cys Gln Ser Leu Thr Arg Thr Val Cys Ala Gly Gly Cys
210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Gln Tyr Ile Lys Ala Asn Ser Lys Phe Ile Gly Ile Thr Glu Leu Arg
            275                 280                 285

Tyr Thr Phe Gly Ala Ser Cys Val Thr Ala Cys Pro Tyr Asn Tyr Leu
290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
            355                 360                 365

Lys Ile Phe Gly Ser Leu Ala Phe Leu Pro Glu Ser Phe Asp Gly Asp
370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
            435                 440                 445

Gly Ile Ser Trp Leu Gly Leu Arg Ser Leu Arg Glu Leu Gly Ser Gly
450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
```

```
                    500             505             510
Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
        530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
                580                 585                 590

Pro Pro Phe Cys Val Ala Arg Cys Pro Ser Gly Val Lys Pro Asp Leu
            595                 600                 605

Ser Tyr Met Pro Ile Trp Lys Phe Pro Asp Glu Glu Gly Ala Cys Gln
            610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Phe Asn Asn
                645                 650                 655

Phe Thr Val Ser Phe Trp Leu Arg Val Pro Lys Val Ser Ala Ser His
                660                 665                 670

Leu Glu Ile Val Ser Ala Val Val Gly Ile Leu
            675                 680
```